United States Patent [19]

Hattori et al.

[11] Patent Number: 4,877,854

[45] Date of Patent: Oct. 31, 1989

[54] CURABLE COMPOSITION

[75] Inventors: Norikazu Hattori, Sagamihara; Sunao Urabe, Yokohama; Koshi Kusumoto, Kamakura, all of Japan

[73] Assignee: Tokuyama Soda Kabushiki Kaisha, Yamaguchi, Japan

[21] Appl. No.: 129,173

[22] Filed: Dec. 7, 1987

[30] Foreign Application Priority Data

Dec. 8, 1986 [JP] Japan .................................. 61-290598
Aug. 7, 1987 [JP] Japan .................................. 62-196377

[51] Int. Cl.$^4$ .............................................. C08G 77/06
[52] U.S. Cl. ........................................ 528/15; 528/31; 528/25; 528/29; 556/479; 523/107; 523/109
[58] Field of Search ....................... 528/15, 25, 29, 31; 556/479; 523/107, 109

[56] References Cited

U.S. PATENT DOCUMENTS 4,593,068  6/1968  Hirose et al. ........................ 525/100
4,617,238 10/1986  Crivello et al. ...................... 528/25
4,735,829  4/1988  Hirose et al. ........................ 525/404

Primary Examiner—Melvyn I. Marquis
Attorney, Agent, or Firm—Sherman and Shalloway

[57] ABSTRACT

A curable composition comprising an unsaturated polyether having terminal alkenyl groups, a linear or branched siloxane-substituted polyether having terminal polyorganosiloxane residues and at least two Si-H groups in the molecule and a catalyst having platinum as the main component has an excellent deep portion curing property and provides a cured body having a good hydrophilic property and a good dimensional reproducibility. This curable composition is especially valuable as a dental impression material.

10 Claims, No Drawings

CURABLE COMPOSITION

BACKGROUND OF THE INVENTION

1. Field of the Invention

The present invention relates to a novel curable composition. More particularly, the present invention relates to a curable composition having excellent curing properties and providing a cured product having a good hydrophilic property and an excellent dimensional reproducibility, which is especially valuable as a dental impression material.

2. Description of the Related Art

A curable composition which is cured at normal temperature to provide a cured body having a rubbery elasticity is widely used as a dental impression material, a sealing material and the like. When this curing composition is used as a dental impression material, in order to increase the affinity with the surfaces of teeth and gingiva for obtaining precise impressions, a cured body of the curable composition is required to have a good hydrophilic property. Furthermore, in this use, the curable composition is required to be excellent in such a curing property that the curable composition is uniformly cured even to a deep portion in a short time (hereinafter referred to as "deep portion curing property"), and a cured body of the curable composition is required to have a good dimensional reproducibility without any plastic deformation at the time of removing the cured body from a mold.

As the curable composition having a good hydrophilic property and being excellent in the deep portion curing property, there has been proposed a composition comprising a polyether having alkenyl groups, a polyorganohydrogen-siloxane having a Si-H group and a platinum complex catalyst (see Japanese patent application laid-open specifications No. 78055/80 and No. 55056/85). Although this composition is excellent in the deep portion curing property and hydrophilic property, the compatibility between the polyether and the polyorganohydrogen-siloxane is poor and a completely cured body is hardly obtained. Accordingly, if this curable composition is used as a dental impression material, plastic deformation is caused when the cured body is removed from a mold, and therefore, a precise impression cannot be obtained. It is considered that the compatibility between the polyether and the polyorganohydrogen-siloxane will be improved by modifying the polyorganohydrogen-siloxane with a polyether. However, in case of this composition, since the free terminals of the polyether used for modification acts as a plasticizer in the cured body, the surface of the cured body becomes sticky and there is a risk of occurrence of plastic deformation, and therefore, the composition cannot be practically used. In short, a satisfactory curable composition has not been developed.

SUMMARY OF THE INVENTION

We made research with a view to developing a curable composition having an excellent deep portion curing property and providing a cured body having a good hydrophilic property and a good dimensional reproducibility, and as the result, it was found that this object can be attained by a composition comprising a linear or branched unsaturated polyether having alkenyl groups at the terminal, a linear or branched siloxane-substituted polyether having a polyorganosiloxane at the terminal and at least two Si-H groups in the molecule and a catalyst comprising platinum as the main component. We have now completed the present invention based on this finding.

More specifically, in accordance with the present invention, there is provided a curable composition, which comprises (A) an unsaturated polyether represented by the following general formula:

(I)

wherein A stands for a saturated hydrocarbon group having a valency of 2 to 6, said saturated hydrocarbon group having 1 to 10 carbon atoms, $R_1$ stands for a linear or branched alkylene group having 1 to 6 carbon atoms, with the proviso that if a is 2 or more, each $R_1$ may be the same or a different alkylene group, a is an integer of from 1 to 300, b is an integer of from 2 to 6, and B stands for an unsaturated group represented by the formula

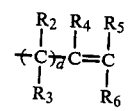

in which $R_2$, $R_3$, $R_4$, $R_5$ and $R_6$, which may be the same or different, stand for a hydrogen atom or an alkyl group having 1 to 10 carbon atoms and d is an integer of from 1 to 10, with the proviso that each B may be the same or a different group;

(B) a siloxane-substituted polyether represented by the following general formula:

(II)

wherein D stands for a saturated hydrocarbon group having a valency of 2 to 6, said saturated hydrocarbon group having 1 to 10 carbon atoms, $R_7$ stands for a linear or branched alkylene group having 1 to 6 carbon atoms, with the proviso that if e is 2 or more, each $R_7$ may be the same or a different alkylene group, e is an integer of from 1 to 30, f is an integer of from 2 to 6, E stands for an alkylene group of the formula

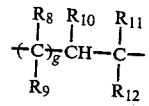

in which $R_8$, $R_9$, $R_{10}$, $R_{11}$ and $R_{12}$, which may be the same or different, stand for a hydrogen atom or an alkyl group having 1 to 10 carbon atoms, and g is an integer of from 1 to 10, with the proviso that each E may be the same or a different alkylene group, and G stand for a siloxane group selected from the group consisting of (i)

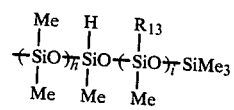

in which h and i are integers of from 0 to 8 satisfying the requirement of h+i=1 to 8, $R_{13}$ stands for a hydrogen atom or a methyl group, with the proviso that if i is 2 or more, each $R_{13}$ may be the same or a different group, and Me stands for a methyl group, (ii)

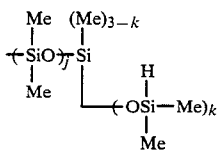

in which j is an integer of from 0 to 8, k is integer of from 1 to 3, with the proviso that j and k satisfy the requirement of j+k=1 to 9, and Me stands for a methyl group, and (iii)

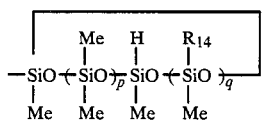

in which p and q are integers of from 0 to 4 satisfying the requirement of p+q=1 to 4 and $R_{14}$ has the same meaning as that of $R_{13}$, with the proviso that each G may be the same or a different siloxane group, and (C) at least one catalyst selected from the group consisting of platinum, chloroplatinic acid and platinum complexes.

Incidentally, in the present invention, the valency of each of A and D in the above-mentioned general formulae (I) and (II) indicates the number of substituents of the saturated hydrocarbon group, and the terminal of each of the polyethers of the general formulae (I) and (II) is a terminal having at least two —OR— bonds (in which R stands for an alkylene group).

DETAILED DESCRIPTION OF THE PREFERRED EMBODIMENTS

The first component of the curable composition is an unsaturated polyether represented by the following general formula:

$$A\mathrm{\{(O-R_1)_aOB\}}_b \quad (I)$$

In the above-mentioned general formula (I), A stands for a saturated hydrocarbon group having a valency of 2 to 6 and 1 to 10 carbon atoms. As defined hereinbefore, the valency of A indicates the number of substituents of the saturated hydrocarbon group. Namely, the saturated hydrocarbon group can have at least 2 substituents and up to 6 substituents. If the number of the substituents exceeds 6, when curable composition of the present invention is cured, a rubbery elasticity cannot be given to the resulting cured body. It is especially preferred that the number of the substituents, that is, the valency of A, be 2 or 3 and the carbon atom number of the saturated hydrocarbon group be 2 to 4. The position of the carbon atom of the saturated hydrocarbon group, on which the substituent is present, is not particularly critical. However, in the case where the carbon atom number is at least 2, the presence of at least 2 substituents on one carbon atom is not preferred from the viewpoint of the stability.

In the above-mentioned general formula (I), $R_1$ stands for a linear or branched alkylene group having 1 to 6 carbon atoms, preferably 2 to 4 carbon atoms. In the case where a in the general formula (I) is 2 or more, $R_1$ may be the same of different alkylene groups each other. Furthermore, in the general formula (I), a is an integer of from 1 to 300 and b is an integer of from 2 to 6. Accordingly, if a is 2 or more, the average degree of polymerization of units —O—$R_1$— is indicated by a, and in this case, the polyether chain comprising units —O—$R_1$— can be in the form of either a random polymer or a block polymer.

In the general formula (I), B stands for an unsaturated group represented by the following formula:

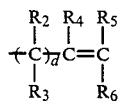

wherein $R_2$, $R_3$, $R_4$, $R_5$ and $R_6$, which may be the same or different, stand for a hydrogen atom or an alkyl group having 1 to 10 carbon atoms, and d is an integer of from 1 to 10, and B may be the same or different unsaturated groups each other. When $R_2$ through $R_6$ stand for an alkyl group, alkyl groups having 1 to 4 carbon atoms, that is, methyl, ethyl, propyl and butyl groups, are preferably used.

As is apparent from the foregoing illustration, the polyether represented by the general formula (I) is an unsaturated polyether having at least 2 alkenyl groups at the terminal. The presence of at least 2 alkenyl groups at the terminal is an important factor for causing curing by crosslinking reaction with the siloxane-substituted polyether of the general formula (II) described hereinafter.

When the curable composition of the present invention is used, for example, as a dental impression material, in order to avoid the irritation to the living body and the volatilization, it is preferred that the molecular weight of the unsaturated polyether be at least 200, and in order to handle the unsaturated polyether in the form of a liquid, it is preferred that the molecular weight of the unsaturated polyether be up to 20,000. The unsaturated polyether is a known compound and can be easily prepared according to a known method. For example, there can be mentioned a method in which a terminal hydroxyl group of a commercially available polyether is reacted with a compound having an alkenyl group and an active group capable of reacting with the above-mentioned hydroxyl group, such as a halogen group, under known conditions. Such known unsaturated polyethers can be used without any limitation.

Typical instances of the unsaturated polyether preferably used in the present invention are described below:

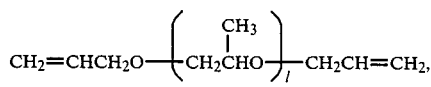

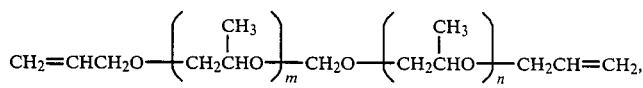

-continued
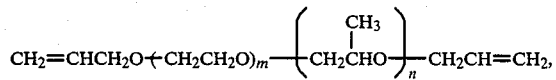
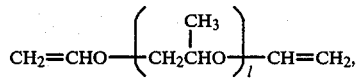
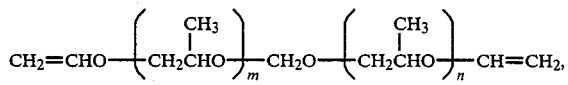
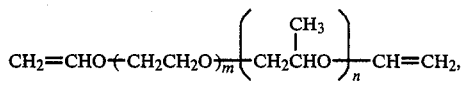
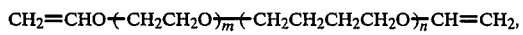
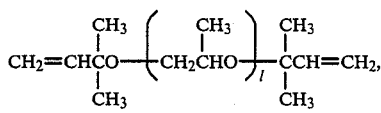
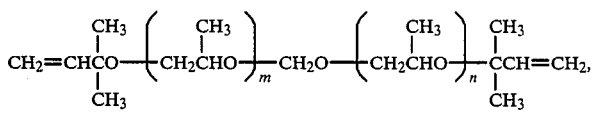
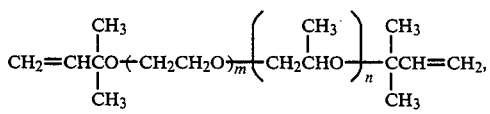
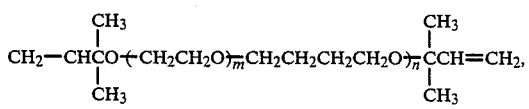
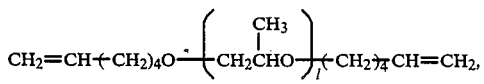
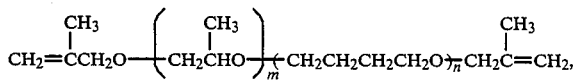
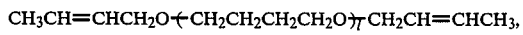
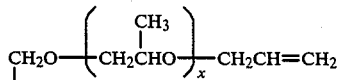
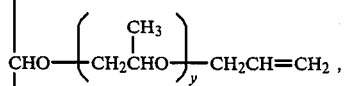
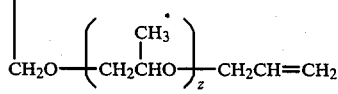

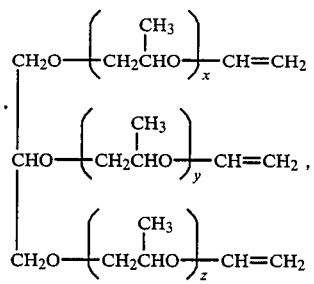
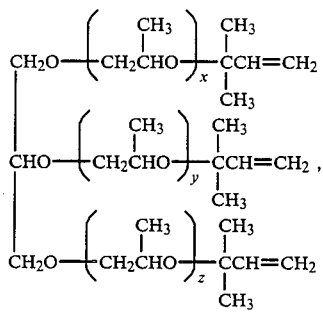
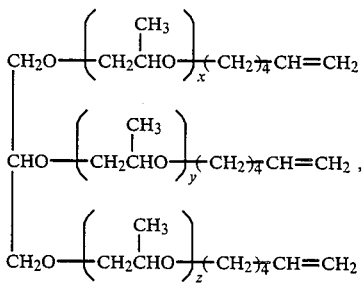
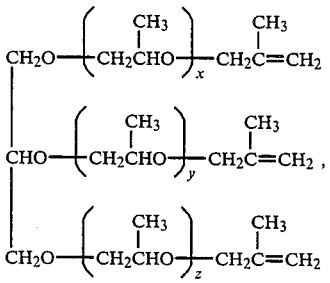
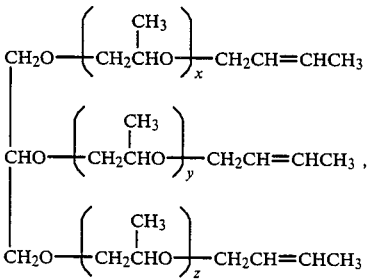

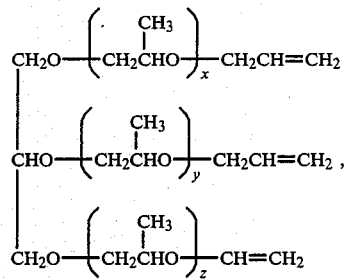
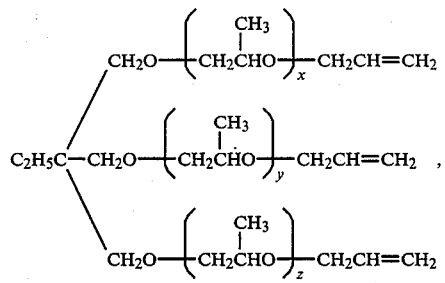
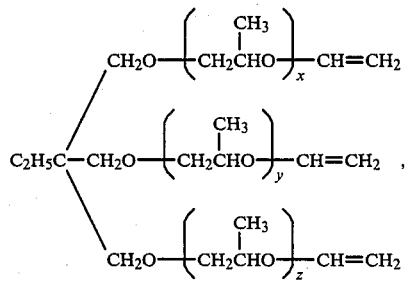
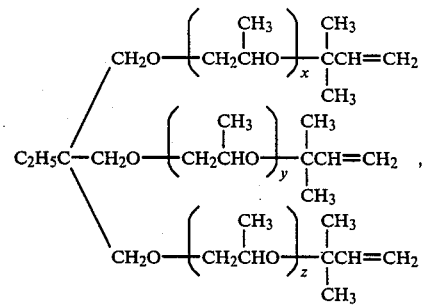
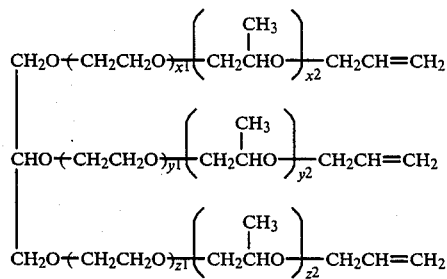
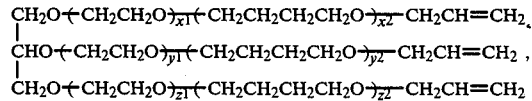

-continued

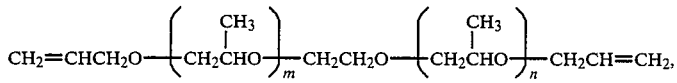

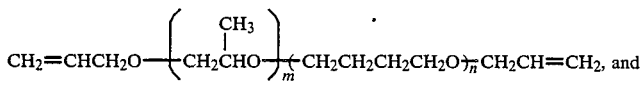

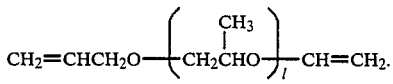

In the above-mentioned formulae, l is an integer of from 3 to 250, m, n, x, y and z are integers of at least 1 and x1, y1, z1, x2, y2 and z2 are integers of at least 0, with the proviso that the sum of m and n is from 3 to 250, the sum of x, y and z is from 3 to 250, the sum of x1 and x2 is at least 1, the sum of y1 and y2 is at least 1 the sum of z1 and z2 is at least 1 and the sum of x1, x2, y1, y2, z1 and z2 is up to 250.

Unsaturated polyethers formed by bonding alkenyl groups to a polyether chain having 2 or 3 terminals have been illustrated hereinbefore, but the unsaturated polyether that can be used in the present invention is not limited to these unsaturated polyethers. For example, unsaturated polyethers formed by bonding alkenyl groups to a polyether chain having 4 to 6 terminals can be used. Furthermore, a mixture of two or more of the above-mentioned unsaturated polyethers can be used.

In view of the easiness of the industrial preparation and the handling easiness, polyethers having allyl groups bonded to both the terminals, which are represented by the following general formula:

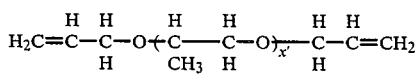

wherein x' is an integer of from 5 to 200, are especially preferred as the unsaturated polyether.

The second component of the curing composition of the present invention is a siloxane-substituted polyether represented by the following general formula:

$$D[(O-R_7)_e O-E-G]_f \quad (II)$$

In the above-mentioned general formula (II), D stands for a saturated hydrocarbon group having a valency of 2 to 6, preferably 2 to 3, and having 1 to 10 carbon atoms, preferably 2 to 4 carbon atoms, as A in the above-mentioned general formula (I). If the valency exceeds 6, when the curable composition of the present invention is cured, a rubbery elasticity cannot be given to the resulting cured body.

In the general formula (II), $R_7$ stands for a linear or branched alkylene group having 1 to 6 carbon atoms, preferably 2 to 4 carbon atoms, as $R_1$ in the general formula (I). If e is 2 or more, each $R_7$ may be the same or a different alkylene group. Accordingly, when e is 2 or more, the polyether chain comprising units $—O—R_7—$ can be in the form of either a random polymer or a block polymer.

In the general formula (II), E stands for an alkylene group represented by the following formula:

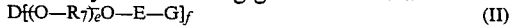

wherein $R_8$, $R_9$, $R_{10}$, $R_{11}$ and $R_{12}$, which may be the same or different, stand for a hydrogen atom or an alkyl group having 1 to 10 carbon atoms and g is an integer of from 1 to 10, and each E may be the same or a different alkylene group. $R_8$, $R_9$, $R_{10}$, $R_{11}$ and $R_{12}$ in the above-mentioned formula may be the same or different and stand for a hydrogen atom or an alkyl group having 1 to 10 carbon atoms, preferably 1 to 4 carbon atoms, as $R_2$ through $R_6$ in the formula representing B in the general formula (I).

In the general formula (II), e is an integer of from 1 to 30, preferably from 1 to 10, and f is an integer of from 2 to 6, preferably from 2 to 3.

In the general formula (II), G stands for a siloxane group represented by the following formula (i), (ii) or (iii):

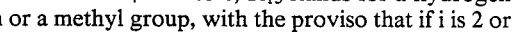

wherein h and i are integers of from 0 to 8 satisfying the requirement of h+i=1 to 8, $R_{13}$ stands for a hydrogen atom or a methyl group, with the proviso that if i is 2 or more, each $R_{13}$ may be the same or a different group, and Me stands for a methyl group,

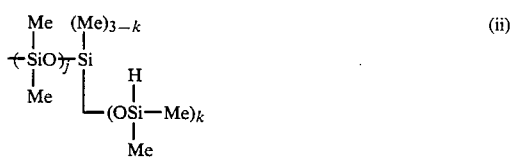

wherein j is an integer of from 0 to 8, k is an integer of from 1 to 3, with the proviso that j and k satisfy the requirement of j+k=1 to 9, and Me stands for a methyl group, or -continued

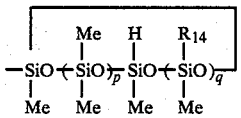
(iii)

wherein p and q are integers of from 0 to 4 satisfying the requirement of p+q=1 to 4, and $R_{14}$ has the same meaning as that of $R_{13}$, and G may be the same or different siloxane groups each other.

The siloxane group represented by the formula (iii) is especially preferred because the curable composition of the present invention exerts an excellent effect when the composition is used as a dental impression material.

When the curable composition is used as a dental impression material, it is preferable to avoid the irritation to the living body and the volatilization. From this viewpoint, it is preferred that the molecular weight of the siloxane-substituted polyether be at least 400. In order to handle the siloxane-substituted polyether in the form of a liquid, it is preferred that the molecular weight be up to 25,000.

Typical instances of the siloxane-substituted polyether preferably used in the present invention are described below:

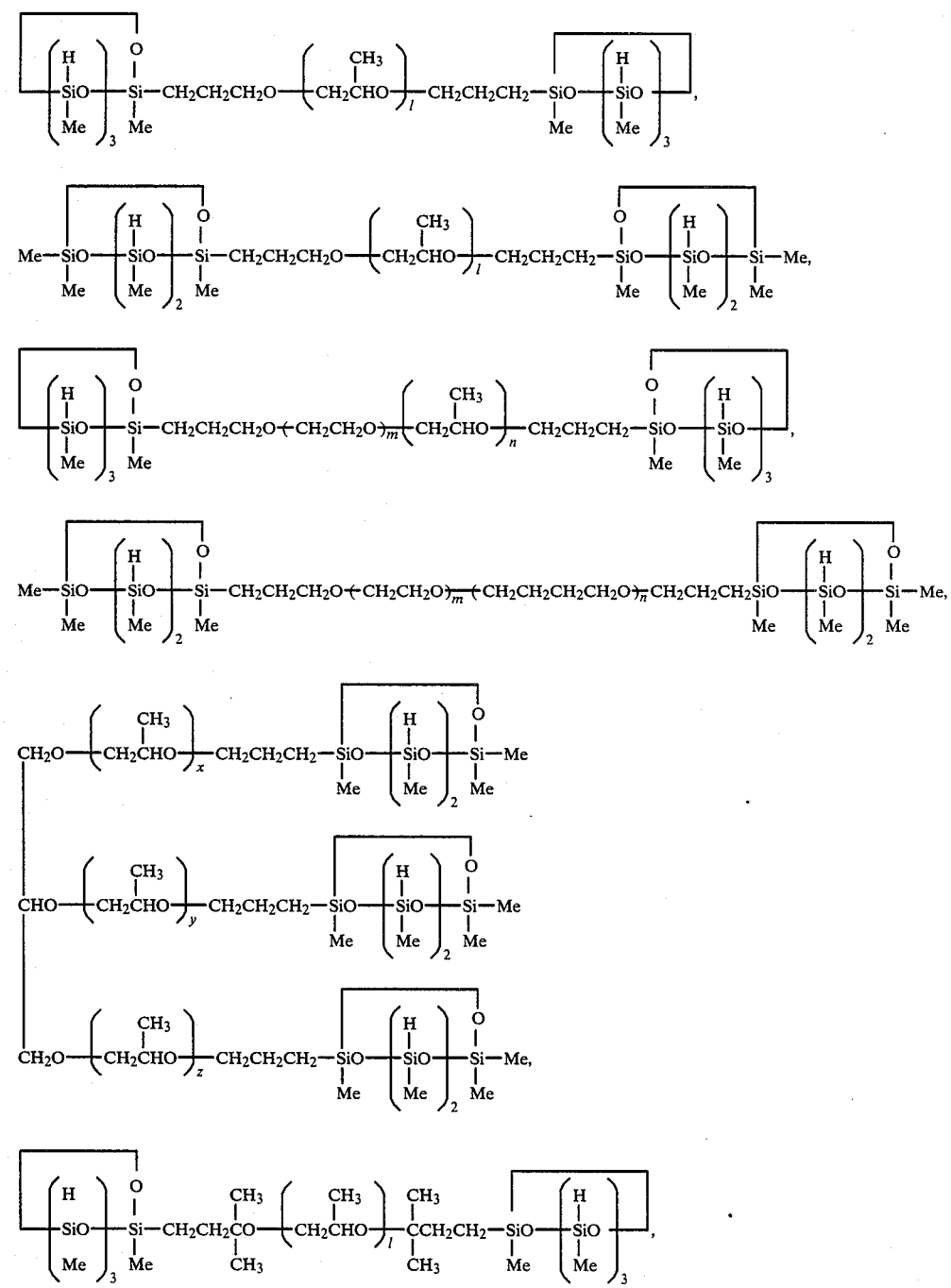

-continued
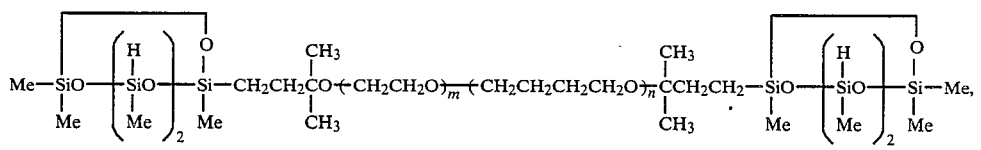
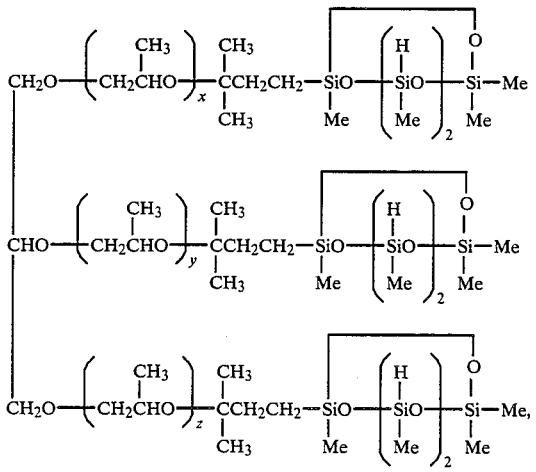
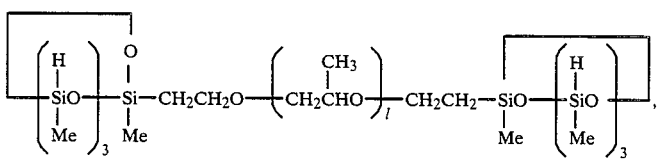
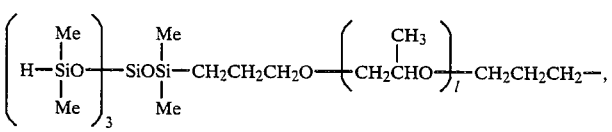
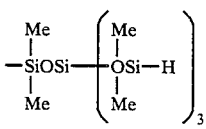
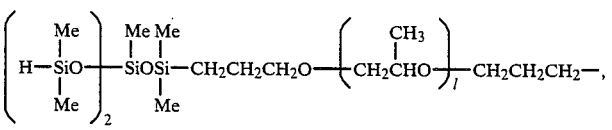
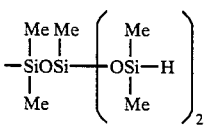

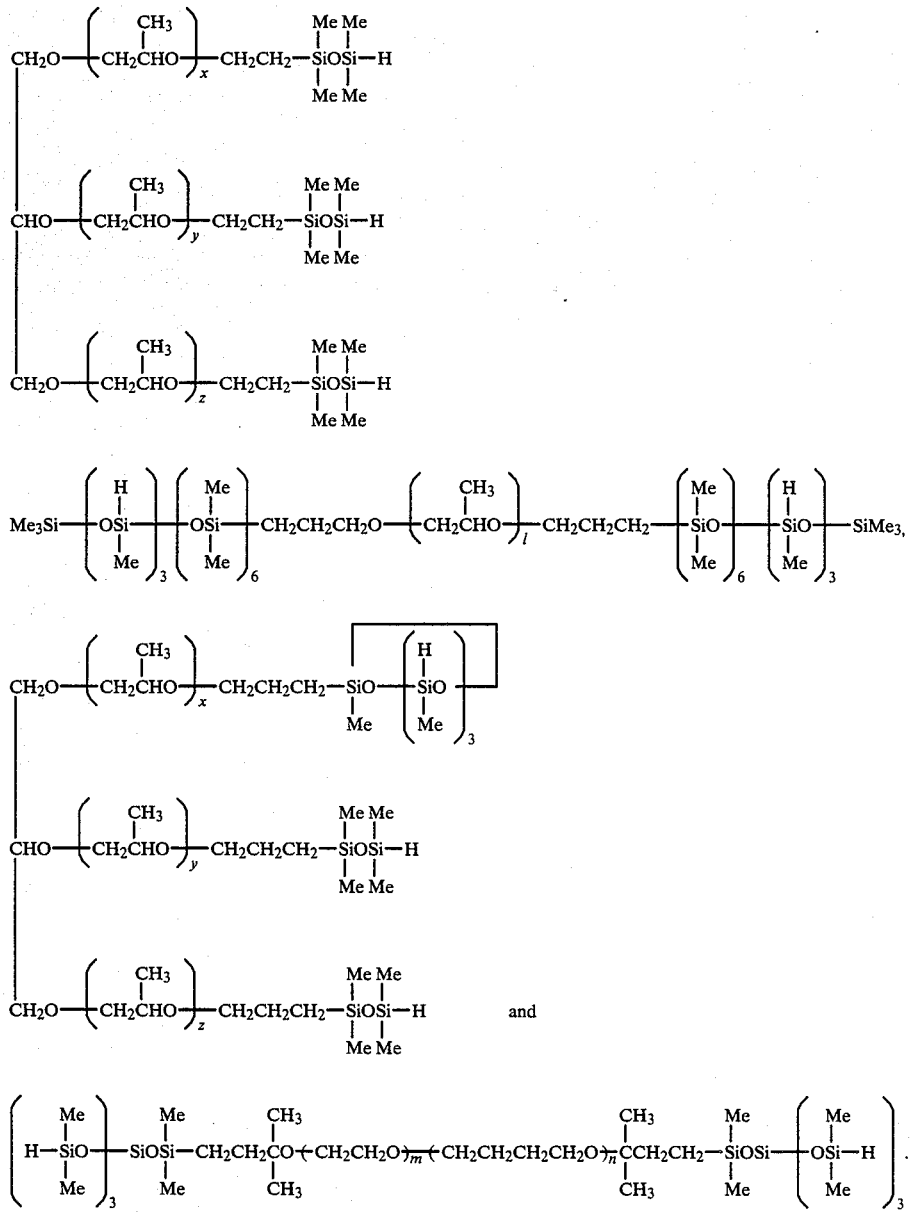

In the above-mentioned formulae, l is an integer of from 3 to 60 and m, n, x, y and z are integers of at least 1, with the proviso that the sum of m and n is from 3 to 60 and the sum of x, y and z is from 3 to 90.

Siloxane-substituted polyethers formed by bonding siloxane groups to a polyether chain having 2 or 3 terminals have been illustrated, but in the present invention, the siloxane-substituted polyether is not limited to these siloxane-substituted polyethers. For example, siloxane-substituted polyethers formed by bonding siloxane groups to a polyether chain having 4 to 6 terminals can be similarly used. Furthermore, a mixture of two or more of the above-mentioned siloxane-substituted polyethers can be used.

In view of the easiness of the industrial preparation and the handling easiness, a siloxane-substituted polyether represented by the following general formula is especially preferred:

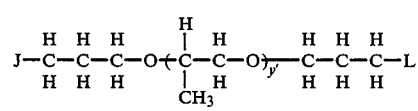

wherein y' is an integer of from 3 to 50, and J and L, which may be the same or different, stand for a group represented by the following formula:

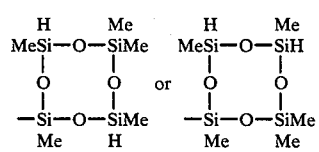

in which Me stands for a methyl group.

Since the siloxane-substituted polyether has a very good compatibility with the unsaturated polyether in the curable composition of the present invention, a uniformly cured body can be obtained, and since siloxane groups are bonded to the terminals of the polyether chain and free terminals of the polyether are hardly present, the plasticizing action of the free terminals of the polyether is not manifested and a cured body having a good dimensional reproducibility.

The siloxane-substituted polyether can be easily prepared according to a known method. For example, the siloxane-substituted polyether is obtained by reacting the above-mentioned unsaturated polyether with a polyorgano-siloxane having at least two Si-H groups in the presence of a platinum catalyst such as chloroplatinic acid so that the molar ratio of the polyorganosiloxane molecule to the alkenyl group is at least 1. In the present invention, even if a product containing an unreacted alkenyl group is left in the siloxane-substituted polyether because of incompleteness of the preparation reaction, since this alkenyl group acts as a crosslinking group in the curable composition, this siloxane-substituted polyether can be used without any trouble. However, since the siloxane-substituted polyether obtained according to the above-mentioned method contains the platinum catalyst, the storage stability is poor, and if the siloxane-substituted polyether is stored for a long time, the Si-H group is decomposed and reacted to cause such troubles as increase of the viscosity and gelation. This disadvantage can be eliminated if the catalyst-containing siloxane-substituted polyether obtained according to the above-mentioned preparation method is contacted with a solid basic substance such as sodium hydrogencarbonate to effect a purifying treatment for removing the platinum catalyst by neutralization and decomposition. Moreover, a method in which the siloxane-substituted polyether is contacted with an adsorbent such as silica gel to remove the platinum catalyst by adsorption is effective.

The third component of the curable composition of the present invention is at least one catalyst selected from the group consisting of platinum, chloroplatinic acid and platinum complexes. This catalyst component is known and widely used, and in the present invention, known catalysts are appropriately selected and used without any limitation. In general, a known catalyst for the hydrosilylation is used. As typical instances of the platinum complex preferably used in the present invention, there can be mentioned a platinum-olefin complex, a complex obtained by reaction between chloroplatinic acid and a vinyl group-containing polysiloxane, and a platinum-phosphorus complex.

The curable composition of the present invention is formed by appropriately mixing the unsaturated polyether, the siloxane-substituted polyether and the platinum catalyst, and the addition order and mixing method are not particularly critical. It is generally preferred that the mixing ratio between the siloxane-substituted polyether and the unsaturated polyether be determined so that the amount of the Si-H groups in the siloxane-substituted polyether is 0.5 to 10 moles per mole of the unsaturated groups in the curable composition. If the molar ratio of the above-mentioned Si-H groups is lower than 0.5, the unsaturated groups become excessive, and therefore, after the curing, large quantities of uncrosslinked polyether chains having unreacted unsaturated groups are left and the dimensional reproducibility of the obtained cured body is often degraded. If the molar ratio of the Si-H groups exceeds 10, the dimensional reproducibility of the obtained cured body is degraded and the object of the present invention cannot be attained. In the field where a high dimensional reproducibility is required, for example, when the curable composition is used as a dental impression material, it is preferred that the molar ratio of the Si-H groups be from 0.8 to 5, especially from 0.9 to 2. The quantity of the Si-H groups can be determined according to a known method. For example, there may be adopted a method in which the sample is dissolved in isopropyl alcohol, potassium hydroxide is added to the solution and the quantity of the Si-H groups is calculated from the amount of generated hydrogen gas. Furthermore, the quantity of the unsaturated groups in the curable composition can be determined according to a known method. For example, the quantity of the unsaturated groups is generally measured according to the method for determination of the total unsaturation degree, specified in JIS K-1557. Moreover, the quantity of the Si-H group and the quantity of the unsaturated groups can be calculated from the theoretical average composition formula derived from the structures of the starting materials used for the preparation of the unsaturated polyether and siloxane-substituted polyether.

In the curable composition of the present invention, the amount of the platinum catalyst is preferably selected so that the amount of the platinum atom in the catalyst is 0.1 ppm to 5% by weight, especially 0.1 to 1,000 ppm, based on the total amount of the unsaturated polyether and siloxane-substituted polyether. If the amount of the platinum atom is smaller than the lower limit, it sometimes happens that the curing reaction is hardly advanced. Even if the amount of the platinum atom exceeds the upper limit, no substantial increase of the effect is attained, and the upper limit is generally determined from the economical viewpoint.

In order improve the operation adaptability before the curing or improve the physical properties after the curing, known inorganic and organic fillers can be added to the curable composition of the present invention. As the inorganic filler, there can be mentioned, for example, fumed silica, pulverized silica, diatomaceous earth, quartz powder, glass fiber, carbon black, iron oxide, zinc oxide, titanium oxide, alumina, magnesia, calcium carbonate, magnesium carbonate and zinc carbonate. As the organic filler, there can be mentioned pulverized polymers and powdery polymers. Since the Si-H groups cause dehydrogenation condensation in an alkaline atmosphere, preliminary addition of an alkaline filler such as magnesia, calcium carbonate or magnesium carbonate to the siloxane-substituted polyether should be avoided. The inorganic filler may be directly used, or it may be used after the surface is treated with a silane coupling agent or the like. The amount added of the filler is not particularly critical, so far as the properties of the obtained cured body are not drastically degraded. In general, it is preferred that the filler be incorporated in an amount of uP to 500 parts by weight per 100 parts by weight of the sum of the unsaturated polyether and siloxane-substituted polyether. If the amount of hydrogen atoms in the Si-H groups is relatively large to the amount of the unsaturated groups in the curable composition of the present invention, hydrogen gas is often generated as a by-product at the curing step. In this case, in order to prevent roughening of the surface of the obtained cured body of this hydrogen gas, it is preferred that a powder of a metal such as palladium, platinum, nickel, magnesium or zinc or a carrier having such a metal atom supported thereon can be added as a hydrogen absorber. The hydrogen absorber is preferably added in such an amount that the amount of the metal atom is 0.1 to 100 ppm based on the total curable composition.

Other additives may be incorporated in the curable composition of the present invention, so far as the physical properties of the obtained cured body are not drastically degraded. As the additive, there can be mentioned a plasticizer, a pigment, an antioxidant, a parting agent and a tackifier.

The curable composition of the present invention is cured at room temperature or under heating. The curable composition of the present invention, which is of the room temperature-curing type, is preferably stored in the form of a two-pack composition in which a mixture of the unsaturated polyether and the catalyst is stored in one pack and the siloxane-substituted polyether or a mixture of the siloxane-substituted polyether and the unsaturated polyether is stored in the form of another pack, and when the composition is practically used, appropriate amounts of both the packs are mixed. If the curing composition is of the heating-curable type, the composition can be stored in the form of the above-mentioned two-pack composition or in the form of a so-called one-pack composition in which the three components are mixed in advance. In view of the durability of the polyether chains, it is preferred that the heating temperature be lower than 150° C. at the time of curing the one-pack composition.

The curable composition of the present invention has an excellent deep portion curing property, and the cured body formed from the composition has a good hydrophilic property, a good dimensional reproducibility and a good dimensional stability. More specifically, since curing of the curable composition of the present invention is advanced by the action of the catalyst, the curable composition is uniformly cured irrespectively of a shallow portion or a deep portion. Moreover, since the composition is composed mainly of the polyether chains, the cured body has a good hydrophilic property. Furthermore, since unsaturated groups or Si-H groups are present on all the terminals of the polyethers in the composition of the present invention, by adjusting the molar ratio between the unsaturated groups, and Si-H groups, the amount of the polyether chains having a free terminal acting as a plasticizer in the cured body can be drastically reduced, and therefore, the surface of the cured body does not become sticky, and plastic deformation is hardly caused and a good dimensional reproducibility is attached. Still in addition, since the curing reaction is addition reaction of the Si-H groups to the unsaturated groups, curing is promptly completed and no dissociative component is generated, and therefore, the dimensional stability with the lapse of time is good.

The curable composition of the present invention having the above-mentioned characteristics can be widely used in various fields, and is especially valuably used as a dental impression material. Furthermore, since the affinity with the living body is enhanced because of a good hydrophilic property and other characteristics, the curable composition of the present invention is valuably used not only as a dental impression material but also as a fit checker or a soft denture reliner.

The present invention will now be described in detail with reference to the following examples that by no means limit the scope of the invention.

Incidentally, in the following examples and comparative examples, the hydrophilic property and dimensional reproducibility of the cured body were determined according to the following methods.

(1) Hydrophilic Property

In a room in which the temperature was adjusted to 23° C. and the relative humidity was adjusted to 50%, 10 μl of pure water was dropped on a smooth surface of the cured body, and after 15 minutes, the contact angle with water was measured by a contact angle measuring device. The closer to 0° C. is the measured value, the higher is the hydrophilic property, and the closer to 90° or more large value is the measured value, the lower is the hydrophilic property.

(2) Dimensional Reproducibility

A columnar cured body having a diameter of 13 mm and a height of 20 mm was used as a test piece, and a compression strain of 12% was imposed on the test piece in the height direction for 30 seconds. When 1 minute had passed from the point of removal of the load, the height h (mm) of the test piece was measured. The compression set was calculated from this value h according to the following formula:

$$\text{compression set} = \frac{20 - h}{20} \times 100\ (\%)$$

The smaller is this value, the better is the dimensional reproducibility, and the larger is this value, the more conspicuous is the plastic deformation.

Furthermore, the molar ratio of (the amount of Si-H groups in the siloxane-substituted polyether)/(the total amount of unsaturated groups in the curable composition) is abbreviated as "Si-H/AL ratio", and the ratio of the platinum atom in the catalyst to the total amount of the unsaturated polyether and the siloxane-substituted polyether is abbreviated as "Cpt".

In the following examples, the average formula of the unsaturated polyether or the siloxane-substituted polyether is a structural formula derived from the structure and composition of the starting materials of the polyether determined according to the chemical analysis (determination of the amounts of the unsaturated groups and Si-H groups and determination of the molecular weight and molecular weight distribution by the liquid chromatography, infrared spectroscopic analysis and nuclear magnetic resonance spectrum), which indicates a structure of the polyether that be averaged.

In the examples and comparative examples, all of "parts" are by weight unless otherwise indicated.

EXAMPLE 1

A paste was prepared by mixing 95 parts of an unsaturated polyether represented by the following average formula:

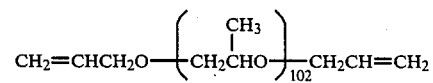

5 parts of a siloxane-substituted polyether (Si-H/AL ratio=1.0) represented by the following average formula:

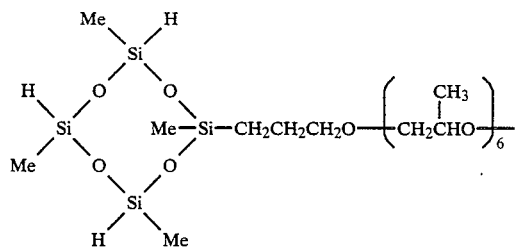

and 100 parts of quartz powder. Then, 0.12 part of a platinum complex (containing 34% by weight of the platinum atom) obtained from chloroplatinic acid and 1,3-divinyl-1,1,3,3-tetramethyldisiloxane (Cpt=400 ppm) was added to the paste and mixed therewith. After 5 minutes at room temperature, a cured body having a rubbery elasticity was obtained. The contact angle of the cured body with water was 53° and the compression set was 0.35%.

EXAMPLE 2

A paste was prepared by mixing 44 parts of an unsaturated polyether represented by the following average formula:

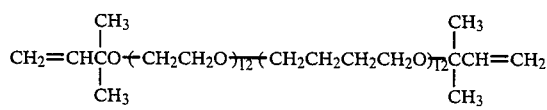

56 parts of a siloxane-substituted polyether (Si-H/AL ratio=1.0) represented by the following formula:

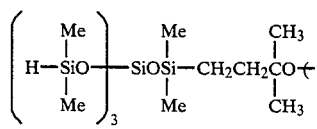

and 10 parts of fumed silica. Then, 0.1 part (Cpt=340 ppm) of the same platinum complex as used in Example 1 was added to the paste and mixed therewith. After 6 minutes at room temperature, a cured body having a rubbery elasticity was obtained. The contact angle of the cured body with water was 31° and the compression set was 0.25%.

EXAMPLE 3

A paste was prepared by mixing 48 parts of an unsaturated polyether represented by the following average formula:

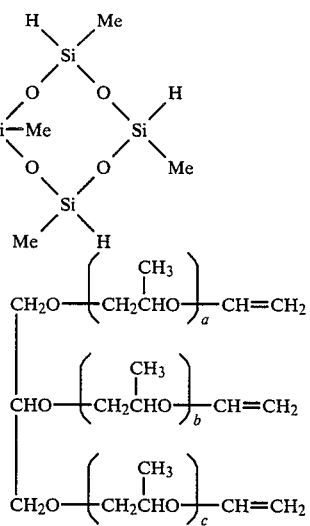

wherein a, b and c are integers of at least 0 satisfying the requirement of $a+b+c=66$, 52 parts of a siloxane-substituted polyether (Si-H/AL Ratio=1.0) represented by the following average formula:

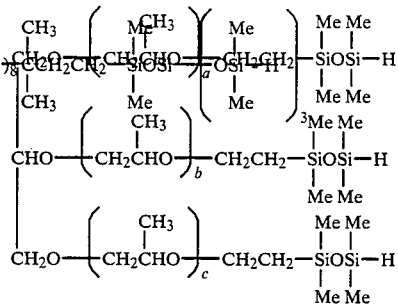

wherein a, b and c are as defined above, and 25 parts by diatomaceous earth. Then, 0.05 part (Cpt=300 ppm) of a platinum complex represented by $PtC_2(C_2H_4)_2$ was added to the paste and mixed therewith. After 7 minutes at room temperature, a cured body having a rubbery elasticity was obtained. The contact angle of the cured body with water 49° and the compression set was 0.37%.

EXAMPLE 4

A paste was prepared by mixing 45 parts of the same unsaturated polyether as used in Example 1, 5 parts of the same siloxane-substituted polyether as used in Example 1, 49.98 parts of quartz powder and 0.02 part of 2,6-di-t-butyl-4-methylphenol (hereinafter referred to as "BHT") as an antioxidant. Separately, a catalyst paste was prepared by mixing 50 parts of the same unsaturated polyether as used in Example 1, 0.12 parts of the same platinum complex as used in Example 1, 49.72 parts of calcium carbonate, 0.02 part of BHT, 0.01 part of 0.5% palladium-supporting alumina and 0.01 part of a red pigment. Both the pastes were stored at room temperature for 1 month, and equal amounts of both the pastes were mixed and kneaded (Si-H/AL ratio=1.0, Cpt=400 ppm), and after 5 minutes at room temperature, a cured body having a rubbery elasticity was obtained. The contact angle of the cured body with water was 54° and the compression set was 0.30%.

EXAMPLE 5

A paste was prepared by mixing 95 parts of the same unsaturated polyether as used in Example 1, 5 parts of the same siloxane-substituted polyether as used in Example 1 (Si-H/AL ratio=1.0), 0.01 part (Cpt=15.7 ppm) of platinum tetra-kis(triphenyl phosphite), 97.96 parts of quartz powder, 2 parts of fumed silica, 0.02 part of BHT and 0.01 part of 0.1% palladium-supporting zeolite. The paste was stored at room temperature for 1 month, and the paste was then treated at 120° C. for 1 hour to obtain a cured body having a rubbery elasticity. The contact angle of the cured body with water was 50° and the compression set was 0.15%.

COMPARATIVE EXAMPLE 1

A paste was prepared by mixing 100 parts of a polysiloxane having terminals blocked with vinyl groups, which was represented by the following average following formula:

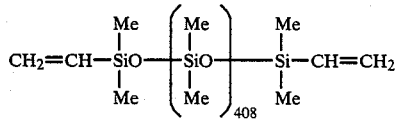

1 part of a polysiloxane (Si-H/AL ratio=1.0) represented by the following average formula:

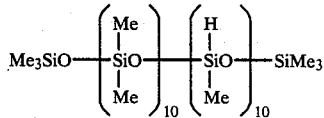

and 100 parts of quartz powder. Then, 0.05 part of the same platinum complex as used in Example 1 (Cpt=168 ppm) was added to the paste and mixed therewith. After 5 minutes at room temperature, a cured body having a rubbery elasticity was obtained. The contact angle of the cured body with water was 73° and the compression set was 0.40%.

COMPARATIVE EXAMPLE 2

A paste was prepared by mixing 91.5 parts of the same unsaturated polyether as used in Example 1, 8.5 parts of a polysiloxane (Si-H/AL ratio=1.0) modified with a polyether represented by the following average formula:

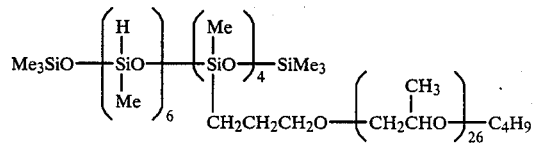

and 100 parts of quartz powder. Then, 0.12 part (Cpt=400 ppm) of the same platinum complex as used in Example 1 was added to the paste and mixed therewith. After 5 minutes at room temperature, a cured body having a rubbery elasticity and a stickiness on the surface was obtained. The compression set of the cured body was 5.60%.

COMPARATIVE EXAMPLE 3

A paste was prepared by mixing 98 parts of the same unsaturated polyether as used in Example 1, 2 parts of 1,3,5,7-tetramethylcyclotetrasiloxane (Si-H/AL ratio=1.0) and 100 parts of quartz powder. This paste was stored at room temperature for 1 month, and 0.12 part (Cpt=400 ppm) of the same platinum complex as used in Example 1 was added to the paste and mixed therewith. Since 1,3,5,7-tetramethylcyclotetrasiloxane had been volatilized during the storage, only the viscosity was increased and no cured body was obtained.

EXAMPLES 6 THROUGH 31

An unsaturated polyether shown in Table 1, siloxane-substituted polyether shown in Table 1 and the same platinum complex as used in Example 1 were mixed so that Si-H/AL ratio and Cpt shown in Table 1 were attained. The curing time at room temperature, the contact angle of the obtained cured body with water and the compression set were measured. The obtained results are shown in Table 1.

In Table 1, x, y and z are integers of at least 1, and $x^1$, $y^1$, $z^1$, $x^2$, $y^2$ and $z^2$ are integers of at least 0, with the proviso that each of $(x^1+x^2)$, $(y^1+y^2)$ and $(z^1+z^2)$ is at least 1. Furthermore, $r^1$, $r^2$, $r^3$, $r^4$, $r^5$ and $r^6$ are integers of at least 1.

TABLE 1

| Example | Unsaturated Polyether | Siloxane-Substituted Polyether | Si—H/AL Ratio | Cpt (ppm) | Curing Time (min) | Contact Angle (°) with Water | Compression Set (%) |
|---|---|---|---|---|---|---|---|
| 6 | $CH_2=CHCH_2O\{CH_2\underset{CH_3}{\underset{|}{C}HO}\}_{51}CH_2O-\{CH_2\underset{CH_3}{\underset{|}{C}HO}\}_{51}CH_2CH=CH_2$ | $Me-\underset{Me}{\underset{|}{Si}}O\{\underset{Me}{\underset{|}{Si}}O\}_2\underset{H}{\underset{|}{Si}}-O-\underset{Me}{\underset{|}{Si}}-CH_2CH_2CH_2O\{CH_2\underset{CH_3}{\underset{|}{C}HO}\}_6$ ... $\{\underset{Me}{\underset{|}{Si}}O\}_2\underset{H}{\underset{|}{Si}}-Me$ | 1.0 | 400 | 5 | 53 | 0.30 |
| 7 | $CH_2=CHCH_2O\{CH_2CH_2O\}_{80}\{CH_2\underset{CH_3}{\underset{|}{C}HO}\}_{20}CH_2CH=CH_2$ | $\{\underset{Me}{\underset{|}{H}SiO}\}_3\underset{Me}{\underset{|}{Si}}-CH_2CH_2CH_2O(CH_2CH_2O)_{20}\{CH_2\underset{CH_3}{\underset{|}{C}HO}\}_5CH_2CH_2CH_2-\underset{Me}{\underset{|}{Si}}\{O\underset{Me}{\underset{|}{Si}}H\}_3$ | 1.0 | 400 | 6 | 22 | 0.35 |
| 8 | $CH_2=CHCH_2O\{CH_2CH_2O\}_{15}$ $\{CH_2CH_2CH_2CH_2O\}_{15}CH_2CH=CH_2$ | $Me-\underset{Me}{\underset{|}{Si}}\{O\underset{Me}{\underset{|}{Si}}H\}_3-CH_2CH_2CH_2O\{CH_2CH_2O\}_{15}$ $\{CH_2CH_2CH_2CH_2O\}_{15}CH_2CH_2CH_2-\underset{Me}{\underset{|}{Si}}\{O\underset{Me}{\underset{|}{Si}}H\}_2$ | 1.0 | 400 | 5.5 | 31 | 0.25 |

TABLE 1-continued

| Example | Unsaturated Polyether | Siloxane-Substituted Polyether | Si—H/AL Ratio | Cpt (ppm) | Curing Time (min) | Contact Angle (°) with Water | Compression Set (%) |
|---|---|---|---|---|---|---|---|
| 9 | $CH_2=CHO\left(\begin{array}{c}CH_3\\|\\-CH_2CHO\end{array}\right)_{51}-CH_2O-$ $-\left(\begin{array}{c}CH_3\\|\\-CH_2CHO\end{array}\right)_{51}-CH=CH_2$ | $CH_2O\left(\begin{array}{c}CH_3\\|\\-CH_2CHO\end{array}\right)_x-CH_2CH_2CH_2-\begin{array}{c}Me\\|\\-SiO\\|\\Me\end{array}\left[\begin{array}{c}O-SiMe\\|\\-SiO-Me\\|\\H\quad Me\end{array}\right]_2$ $CHO\left(\begin{array}{c}CH_3\\|\\-CH_2CHO\end{array}\right)_y-CH_2CH_2CH_2-\begin{array}{c}Me\\|\\-SiO\\|\\Me\end{array}\left[\begin{array}{c}O-SiMe\\|\\-SiO-Me\\|\\H\quad Me\end{array}\right]_2$ $CH_2O\left(\begin{array}{c}CH_3\\|\\-CH_2CHO\end{array}\right)_z-CH_2CH_2CH_2-\begin{array}{c}Me\\|\\-SiO\\|\\Me\end{array}\left[\begin{array}{c}O-SiMe\\|\\-SiO-Me\\|\\H\quad Me\end{array}\right]_2$ | 1.0 | 200 | 7.5 | 54 | 0.15 |
| 10 | $CH_2=CHCO\left(\begin{array}{c}CH_3\\|\\-CH_2CHO\\|\\CH_3\end{array}\right)_{51}-\begin{array}{c}CH_3\\|\\CCH=CH_3\\|\\CH_3\end{array}$ | $\begin{array}{c}CH_3\\|\\-Si-CH_2CH_2CO\\|\\Me\end{array}\left(\begin{array}{c}CH_3\\|\\-CH_2CHO\\|\\CH_3\end{array}\right)_6-\begin{array}{c}CH_3\\|\\CCH_2CH_2-\\|\\CH_3\end{array}$ $\left[\begin{array}{c}O-SiO\\|\\H\quad Me\end{array}\right]_3 \left[\begin{array}{c}-SiO\\|\\Me\end{array}\right]_3-\begin{array}{c}SiO\\|\\Me\end{array}\left[\begin{array}{c}-SiO\\|\\H\quad Me\end{array}\right]_3$ | 1.0 | 500 | 4.5 | 53 | 0.15 |

TABLE 1-continued

| Example | Unsaturated Polyether | Siloxane-Substituted Polyether | Si—H/AL Ratio | Cpt (ppm) | Curing Time (min) | Contact Angle (°) with Water | Compression Set (%) |
|---|---|---|---|---|---|---|---|
| 11 | $CH_2=CH(CH_2)_4O\left(\begin{array}{c}CH_3\\\|\\CH_2CHO\end{array}\right)_{83}(CH_2)_4CH=CH_2$ | $\left[\begin{array}{c}H\\\|\\SiO\\\|\\Me\end{array}\begin{array}{c}O\\\|\\Si\\\|\\Me\end{array}\right]_3$ —$CH_2CH_2CH_2$—$\left(\begin{array}{c}CH_3\\\|\\Si\\\|\\Me\end{array}\begin{array}{c}\\CH_2CH_2CH_2O\left(CH_2CHO\right)_{12}\end{array}\right)$ $\left[-CH_2CH_2CH_2-\underset{Me}{\overset{Me}{\underset{\|}{Si}}}O\left(\underset{Me}{\overset{H}{\underset{\|}{Si}}}O\right)_3\right]$ | 0.7 | 400 | 6.5 | 50 | 0.20 |
| 12 | $CH_2=CCH_2O\left(\begin{array}{c}CH_3\\\|\\CH_2CHO\end{array}\right)_{20}\underset{CH_3}{\overset{}{}}$ $\left(CH_2CH_2CH_2O\right)_{20}CH_2C=CH_2$ | $\left[H-\underset{Me}{\overset{Me}{\underset{\|}{Si}}}O-\underset{CH_3}{\overset{CH_3}{\underset{\|}{Si}}}O-\right]_3$—$CH_2CH_2CO\left(CH_2CH_2O\right)_{12}$—$\left[\begin{array}{c}Me\\\|\\Si\\\|\\CH_3\end{array}\right]$—$CCH_2CH_2SiOSi\left(\begin{array}{c}Me\\\|\\OSi\\\|\\Me\end{array}\begin{array}{c}H\\\|\\\end{array}\right)_3$ | 0.8 | 400 | 6 | 42 | 0.15 |
| 13 | $CH_3CH=CHCH_2O\left(CH_2CH_2-\right.$ $-CH_2CH_2O)_{25}-CH_2CH=CHCH_3$ | $\left[\begin{array}{c}H\\\|\\SiO\end{array}\begin{array}{c}O\\\|\\Si\\\|\\Me\end{array}\right]_3$ —$CH_2CH_2CH_2O\left(\begin{array}{c}CH_3\\\|\\CH_2CHO\end{array}\right)_6CH_2CH_2$— $\left[-SiO\left(\underset{Me}{\overset{H}{\underset{\|}{Si}}}O\right)_3\right]$ | 0.8 | 400 | 6 | 59 | 0.20 |

TABLE 1-continued

| Example | Unsaturated Polyether | Siloxane-Substituted Polyether | Si—H /Al Ratio | Cpt (ppm) | Curing Time (min) | Contact Angle (°) with Water | Compression Set (%) |
|---|---|---|---|---|---|---|---|
| 14 | $CH_2=CHCH_2O\!-\!(CH_2CHO\,\vert\,CH_3)_{51}\!-\!CH_2\!-$ <br> $-CH_2O\!-\!(CH_2CHO\,\vert\,CH_3)_{51}\!-\!CH_2CH=CH_2$ | $\left\{H\!-\!SiO\,\substack{Me\\\vert\\Me}\!SiOSi\!-\!CH_2CH_2CH_2O\!-\!(CH_2CHO\,\vert\,CH_3)_{12}\right\}_3$ <br> $-CH_2CH_2CH_2\!-\!\left\{Si\,\substack{Me\\\vert\\Me}\!-\!OSi\,\substack{Me\\\vert\\Me}\!-\!H\right\}_3$ | 0.9 | 400 | 5.5 | 53 | 0.30 |
| 15 | $CH_2O\!-\!(CH_2CH_2O)_{x^1}\!-\!(CH_2CH_2CH_2\,\vert\,CH_2O)_{x^2}\!-\!CH_2CH=CH_2$ <br> $CHO\!-\!(CH_2CH_2O)_{y^1}\!-\!(CH_2CH_2CH_2\,\vert\,CH_2O)_{y^2}\!-\!CH_2CH=CH_2$ <br> $CH_2O\!-\!(CH_2CH_2O)_{z^1}\!-\!(CH_2CH_2CH_2\,\vert\,CH_2O)_{z^2}\!-\!CH_2CH=CH_2$ <br> $x^1+y^1+z^1=20,\; x^2+y^2+z^2=20$ | $Me\!-\!SiO\,\substack{CH_3\\\vert\\Me}\!-\!Si\!-\!CH_2CH_2CH_2\!-\!\left[\substack{O\\\vert}\!-\!Si\,\substack{Me\\\vert\\Me}\!-\!H\right]_2$ <br> $(CH_2CH_2CH_2O)_6\,CCH_2CH_2\!-\!\left[\substack{O\\\vert}\!-\!Si\,\substack{Me\\\vert\\Me}\!-\!O\!-\!SiO\,\substack{Me\\\vert\\Me}\!-\!Si\!-\!Me\right]_2$ | 0.9 | 400 | 5 | 32 | 0.30 |
| 16 | $CH_2O\!-\!(CH_2CHO\,\vert\,CH_3)_x\!-\!CH_2CH=CH_2$ <br> $CHO\!-\!(CH_2CHO\,\vert\,CH_3)_y\!-\!CH_2CH=CH_2$ <br> $CH_2O\!-\!(CH_2CHO\,\vert\,CH_3)_z\!-\!CH_2CH=CH_2$ <br> $x+y+z=51$ | $\left\{H\!-\!Si\,\substack{Me\,Me\\\vert\quad\vert\\Me}\!-\!OSi\!-\!CH_2CH_2CH_2O\!-\!(CH_2CHO\,\vert\,CH_3)_{12}\right\}_2$ <br> $-CH_2CH_2CH_2\!-\!\left\{Si\,\substack{Me\,Me\\\vert\quad\vert\\Me}\!-\!OSi\,\substack{Me\\\vert\\Me}\!-\!H\right\}_2$ | 1.2 | 400 | 5 | 50 | 0.20 |

TABLE 1-continued

| Example | Unsaturated Polyether | Siloxane-Substituted Polyether | Si—H/AL Ratio | Cpt (ppm) | Curing Time (min) | Contact Angle (°) with Water | Compression Set (%) |
|---|---|---|---|---|---|---|---|
| 17 | $CH_2O$–$(CH_2CH_2O)_{x1}$–$(CH_2CHO(CH_3))_{x2}$–$CH_2CH=CH_2$ <br> $CHO$–$(CH_2CH_2O)_{y1}$–$(CH_2CHO(CH_3))_{y2}$–$CH_2CH=CH_2$ <br> $CH_2O$–$(CH_2CH_2O)_{z1}$–$(CH_2CHO(CH_3))_{z2}$–$CH_2CH=CH_2$ <br> $x^1 + y^1 + z^1 = 80$, $x^2 + y^2 + z^2 = 20$ | $CH_2O$–$(CH_2CH_2O)_{x1}$–$(CH_2CHO(CH_3))_{xT}$–$Si$–$CH_2CH_2CH_2O$–$(CH_2CH_2O)_{70}$ with $[HSiO(Me)_2]_3$ and $SiO$–$Me$ groups <br> $CH_3$–$(CH_2CHO)_5$–$CH_2CH_2CH_2$–$SiO$–$Me$ with $[HSiO(Me)_2]_3$ | 1.5 | 400 | 4.5 | 20 | 0.35 |
| 18 | $CH_2O$–$(CH_2CHO(CH_3))_x$–$CCH_2C(CH_3)_2CH_3$ <br> $CHO$–$(CH_2CHO(CH_3))_y$–$CCH_2C(CH_3)_2CH_3$ <br> $CH_2O$–$(CH_2CHO(CH_3))_z$–$CCH_2C(CH_3)_2CH_3$ <br> $x + y + z = 17$ | $CH_2O$–$(CH_2CHO(CH_3))_x$–$CCH_2C(CH_3)_2CH_3$–$SiO(Me)$–$[HSiO(Me)_2]_2$–$Si(Me)_2$–$O$ <br> $CHO$–$(CH_2CHO(CH_3))_y$–$CCH_2C(CH_3)_2CH_3$–$SiO(Me)$–$[HSiO(Me)_2]_2$–$Si(Me)_2$–$O$ <br> $CH_2O$–$(CH_2CHO(CH_3))_z$–$CCH_2C(CH_3)_2CH_3$–$SiO(Me)$–$[HSiO(Me)_2]_2$–$Si(Me)_2$–$O$ <br> $x + y + z = 10$ | 2.0 | 400 | 3 | 51 | 0.30 |

TABLE 1-continued

| Example | Unsaturated Polyether | Siloxane-Substituted Polyether | Si—H/AL Ratio | Cpt (ppm) | Curing Time (min) | Contact Angle (°) with Water | Compression Set (%) |
|---|---|---|---|---|---|---|---|
| 19 | $\left[CH_2O\left(CH_2CHO\atop{\vert\atop CH_3}\right)_x CH_2CH=CH_2\right]$ $\left[CHO\left(CH_2CHO\atop{\vert\atop CH_3}\right)_y CH_2CH=CH_2\right]$ $\left[CH_2O\left(CH_2CHO\atop{\vert\atop CH_3}\right)_z CH=CH_2\right]$ $x+y+z=66$ | $\left[CH_2O\left(CH_2CHO\atop{\vert\atop CH_3}\right)_x CH_2CH_2CH_2-SiO\!\left(\!{Me\atop\vert}SiO\!\right)_{\!3}\!\!\left[\!H{Me\atop\vert}\!\right]\right]$ $\left[CHO\left(CH_2CHO\atop{\vert\atop CH_3}\right)_y CH_2CH_2CH_2-Si(Me)_2OSi(Me)_2-H\right]$ $\left[CH_2O\left(CH_2CHO\atop{\vert\atop CH_3}\right)_z CH_2CH_2CH_2-Si(Me)_2OSi(Me)_2-H\right]$ $x+y+z=17$ | 2.0 | 400 | 3 | 51 | 0.35 |
| 20 | $\left[CH_2O\left(CH_2CHO\atop{\vert\atop CH_3}\right)_x CH_2CH=CH_2\right]$ $C_2H_5C\!-\!CH_2O\!-\!\left[CH_2O\left(CH_2CHO\atop{\vert\atop CH_3}\right)_y CH_2CH=CH_2\right]$ $\left[CH_2O\left(CH_2CHO\atop{\vert\atop CH_3}\right)_z CH_2CH=CH_2\right]$ $x+y+z=66$ | $Me_3SiO\!-\!\left(\!{Me\atop\vert}SiO\!\right)_{\!6}\!CH_2CH_2CH_2O-$ $\left(\!{H\atop\vert}{Me\atop\vert}SiO\!\right)_{\!3}\!\left(\!{Me\atop\vert}SiO\!\right)_{\!6}CH_2CH_2CH_2\!\left(CH_2CHO\atop{\vert\atop CH_3}\right)_{\!6}\!\left(\!{Me\atop\vert}SiO\!\right)_{\!6}\!\left(\!{H\atop\vert}{Me\atop\vert}SiO\!\right)_{\!3}SiMe_3$ | 3.0 | 400 | 3.5 | 52 | 0.25 |

TABLE 1-continued

| Example | Unsaturated Polyether | Siloxane-Substituted Polyether | Si—H/AL Ratio | Cpt (ppm) | Curing Time (min) | Contact Angle (°) with Water | Compression Set (%) |
|---|---|---|---|---|---|---|---|
| 21 | $CH_2=CHCH_2O\left(CH_2CH(CH_3)O\right)_{10}$ $\left(CH_2CH_2CH_2O\right)_{10}CH_2CH=CH_2$ | $\begin{array}{c} CH_2O\left(CH_2CH(CH_3)O\right)_x-CH_2CH_2CH_2-SiMe_2OSiMe_2-H \\ CHO\left(CH_2CH(CH_3)O\right)_y-CH_2CH_2CH_2-SiMe_2OSiMe_2-H \\ CH_2O\left(CH_2CH(CH_3)O\right)_z-CH_2CH_2CH_2-SiMe_2OSiMe_2-H \end{array}$ $x+y+z=6$ | 1.0 | 80 | 17 | 60 | 0.25 |
| 22 | $CH_2=CHCH_2O\left(CH_2CH(CH_3)O\right)_{102}-CH=CH_2$ | $\begin{array}{c} CH_2O\left(CH_2CH(CH_3)O\right)_x-CH_2CH_2CH_2-SiMe_2O\left(SiMe(H)O\right)_3SiMe_2-H \\ CHO\left(CH_2CH(CH_3)O\right)_y-CH_2CH_2CH_2-SiMe_2OSiMe_2-H \\ CH_2O\left(CH_2CH(CH_3)O\right)_z-CH_2CH_2CH_2-SiMe_2OSiMe_2-H \end{array}$ $x+y+z=17$ | 1.0 | 100 | 11 | 53 | 0.30 |

TABLE 1-continued

| Example | Unsaturated Polyether | Siloxane-Substituted Polyether | Si—H/AL Ratio | Cpt (ppm) | Curing Time (min) | Contact Angle (°) with Water | Compression Set (%) |
|---|---|---|---|---|---|---|---|
| 23 | $CH_2O\!\!-\!\!\!\left(CH_2\overset{CH_3}{\underset{|}{C}HO}\right)_x\!\!-\!\!CH\!=\!CH_2$<br>$CHO\!\!-\!\!\!\left(CH_2\overset{CH_3}{\underset{|}{C}HO}\right)_y\!\!-\!\!CH\!=\!CH_2$<br>$CH_2O\!\!-\!\!\!\left(CH_2\overset{CH_3}{\underset{|}{C}HO}\right)_z\!\!-\!\!CH\!=\!CH_2$<br>$x+y+z=66$ | (siloxane structure) | 1.0 | 800 | 0.5 | 52 | 0.30 |
| 24 | $CH_2O\!\!-\!\!\!\left(CH_2\overset{CH_3}{\underset{|}{C}HO}\right)_x\!\!-\!(CH_2)_4\!\!-\!CH\!=\!CH_2$<br>$CHO\!\!-\!\!\!\left(CH_2\overset{CH_3}{\underset{|}{C}HO}\right)_y\!\!-\!(CH_2)_4\!\!-\!CH\!=\!CH_2$<br>$CH_2O\!\!-\!\!\!\left(CH_2\overset{CH_3}{\underset{|}{C}HO}\right)_z\!\!-\!(CH_2)_4\!\!-\!CH\!=\!CH_2$<br>$x+y+z=35$ | 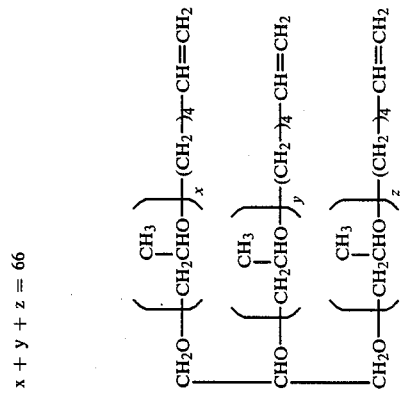 | 1.0 | 600 | 1 | 44 | 0.35 |

TABLE 1-continued
| Example | Unsaturated Polyether | Siloxane-Substituted Polyether | Si—H /AL Ratio | Cpt (ppm) | Curing Time (min) | Contact Angle (°) with Water | Compression Set (%) |
|---|---|---|---|---|---|---|---|
| 25 | same as Example 1 |  | 1.0 | 200 | 5 | 53 | 0.30 |
| 26 |  | 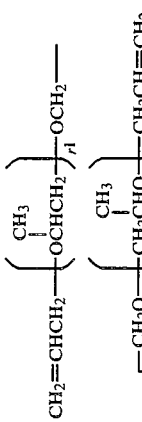 | 1.0 | 300 | 4 | 54 | 0.25 |
| 27 | 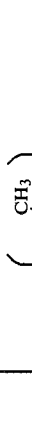 | Same as in Example 26 | 1.0 | 300 | 5 | 53 | 0.20 |

TABLE 1-continued
| Example | Unsaturated Polyether | Siloxane-Substituted Polyether | Si—H /AL Ratio | Cpt (ppm) | Curing Time (min) | Contact Angle (°) with Water | Compression Set (%) |
|---|---|---|---|---|---|---|---|
| 28 | 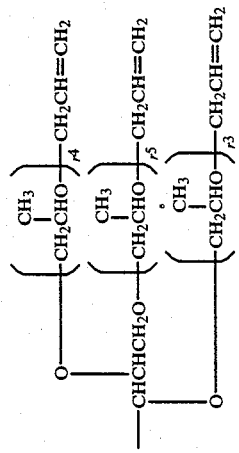<br>$r^1 + r^2 + r^3 + r^4 + r^5 = 120$ | Same as in Example 26 | 1.0 | 300 | 5 | 53 | 0.20 |
| 29 | 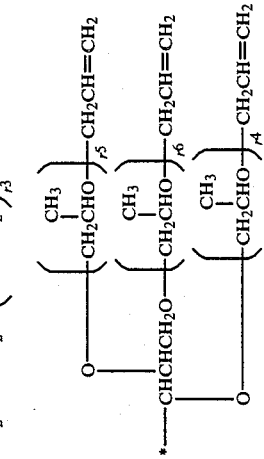<br>$r^1 + r^2 + r^3 + r^4 + r^5 + r^6 = 120$<br>Same as in Example 1 | 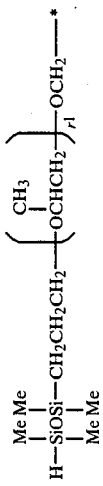 | 1.0 | 300 | 6 | 52 | 0.30 |

TABLE 1-continued

| Example | Unsaturated Polyether | Siloxane-Substituted Polyether | Si—H /AL Ratio | Cpt (ppm) | Curing Time (min) | Contact Angle (°) with Water | Compression Set (%) |
|---|---|---|---|---|---|---|---|
| | | $*{-}C{\Big(}CH_2O{-}{\big(}CH_2CHO{-}\underset{CH_3}{\big|}{-}CH_2CH_2CH_2{-}\underset{Me}{\overset{Me}{SiOSi}}{-}H\underset{Me}{\overset{Me}{\phantom{Si}}}{\big)}_{r^2}{\Big)}_3$ (three branches with $r^2, r^3, r^4$) $r^1 + r^2 + r^3 + r^4 = 120$ | 1.0 | 300 | 6 | 54 | 0.30 |
| 30 | Same as in Example 1 | Structure with $r^1, r^2, r^3, r^4, r^5$; $r^1 + r^2 + r^3 + r^4 + r^5 = 120$ | | | | | |

TABLE 1-continued

| Example | Unsaturated Polyether | Siloxane-Substituted Polyether | Si—H /AL Ratio | Cpt (ppm) | Curing Time (min) | Contact Angle (°) with Water | Compression Set (%) |
|---|---|---|---|---|---|---|---|
| 31 | Same as in Example 1 | (structure shown below) | 1.0 | 300 | 6 | 54 | 0.35 |

$$H-SiOSi-CH_2CH_2CH_2-\left(-\underset{\underset{OCHCH_2}{\overset{CH_3}{|}}}{O}-\right)_{r2}\overset{O}{|}$$

$$\overset{Me\,Me}{|}$$
$$H-SiOSi-CH_2CH_2CH_2-\left(-\underset{\underset{OCHCH_2}{\overset{CH_3}{|}}}{O}-\right)_{r1}OCH_2CHCH-*$$
$$\overset{Me\,Me}{|}$$

$$H-SiOSi-CH_2CH_2CH_2-\left(-\underset{\underset{OCHCH_2}{\overset{CH_3}{|}}}{O}-\right)_{r3}\overset{O}{|}$$
$$\overset{Me\,Me}{|}$$

$$*-CHCH_2O-\left(-\underset{\underset{CH_2CHO}{\overset{CH_3}{|}}}{}-CH_2CH_2CH_2-\underset{Me\,Me}{\overset{Me\,Me}{|}}SiOSi-H\right)_{r4}$$

$$\left(-\underset{\underset{CH_2CHO}{\overset{CH_3}{|}}}{}-CH_2CH_2CH_2-\underset{Me\,Me}{\overset{Me\,Me}{|}}SiOSi-H\right)_{r5}$$

$$\left(-\underset{\underset{CH_2CHO}{\overset{CH_3}{|}}}{}-CH_2CH_2CH_2-\underset{Me\,Me}{\overset{Me\,Me}{|}}SiOSi-H\right)_{r6}$$

$$r^1 + r^2 + r^3 + r^4 + r^5 + r^6 = 120$$

EXAMPLE 32

A paste was prepared in the same manner as described in Example 5 except that 0.08 part (Cpt=800 ppm) of platinum black was used instead of 0.01 part of tetra-kis(triphenyl phosphite). When the paste was treated at 120° C. for 3 hours, a cured body having a rubbery elasticity was obtained. The contact angle of the cured body with water was 50° and the compression set was 0.20%.

EXAMPLE 33

A paste was prepared in the same manner as described in Example 1 except that 0.16 part (Cpt=600 ppm) of chloroplatinic acid was used instead of 0.12 part of the platinum complex. When the paste was mixed at room temperature for 24 hours, a cured body having a rubbery elasticity was obtained. The contact angle of the cured body with water was 53° and the compression set was 0.35%.

EXAMPLES 34 THROUGH 63

Impression materials composed of curable compositions described below were prepared by using the unsaturated polyethers, siloxane-substituted polyethers and catalysts used in Examples 1 through 31 (except 5).

| Paste A | |
|---|---|
| Unsaturated polyether | 50 parts |
| Catalyst (Cpt value obtained when pastes A and B were mixed is shown in Table 2) | |
| Calcium carbonate | 50 parts |
| BHT | 0.02 part |
| 0.5% Palladium-supporting alumina | 0.01 part |
| Paste B | |
| Unsaturated polyether plus siloxane-substituted polyether | 50 parts |
| (Si-H/L ratio in the sum of pastes A and B is shown in Table 2) | |
| Quartz powder | 50 parts |
| BHT | 0.02 part |

Equal amounts of the pastes A and B of the impression material were kneaded, and the curing time, the contact angle with water and the compression set were measured. Furthermore, the compression strain and dimensional change were measured according to the measurement method No. 19 of American Dental Association Specification. Moreover, the impression in the oral cavity was collected by using the above-mentioned impression material. The state of the impression surface was evaluated based on blowing marks and the stickiness. A dental crown was prepared based on the so-obtained impression, and the presicion was evaluated based on the fitness of the crown.

The standards for evaluation of the blowing marks, stickiness and precision are as follows.

(1) Blowing Marks
   A: no mark
   B: some marks
   C: many marks
(2) Stickiness
   A: no stickiness
   B: slight stickiness
   C: strong stickiness
(3) Precision
   A: crown was well fit
   B: crown was slightly unfit
   C: crown was not fit at all The obtained results are shown in Table 2.

Corresponding Examples indicate the numbers of the above-mentioned Examples 1 through 31.

| Example No. | Corresponding Example No. | Si-H/AL Ratio | Cpt (ppm) | Curing Time (minutes) | Contact Angle (°) With Water | Compression Set (%) |
|---|---|---|---|---|---|---|
| 34 | 1 | 1.0 | 200 | 4 | 53 | 0.40 |
| 35 | 2 | 1.0 | 170 | 5 | 32 | 0.35 |
| 36 | 3 | 1.0 | 500 | 4.5 | 50 | 0.30 |
| 37 | 4 | 1.1 | 150 | 6 | 51 | 0.45 |
| 38 | 6 | 1.1 | 150 | 5 | 49 | 0.50 |
| 39 | 7 | 1.0 | 250 | 5 | 21 | 0.55 |
| 40 | 8 | 1.0 | 200 | 5 | 29 | 0.40 |
| 41 | 9 | 0.9 | 150 | 5.5 | 53 | 0.55 |
| 42 | 10 | 1.0 | 160 | 5.5 | 53 | 0.35 |
| 43 | 11 | 1.0 | 160 | 6 | 51 | 0.40 |
| 44 | 12 | 1.0 | 180 | 6 | 44 | 0.40 |
| 45 | 13 | 1.0 | 150 | 5.5 | 58 | 0.35 |
| 46 | 14 | 1.2 | 200 | 5 | 50 | 0.60 |
| 47 | 15 | 1.4 | 220 | 5 | 29 | 0.65 |
| 48 | 16 | 1.0 | 160 | 4.5 | 49 | 0.30 |
| 49 | 17 | 1.0 | 160 | 4 | 21 | 0.25 |
| 50 | 18 | 1.0 | 120 | 5 | 53 | 0.35 |
| 51 | 19 | 1.0 | 130 | 4.5 | 53 | 0.35 |
| 52 | 20 | 0.8 | 150 | 5 | 51 | 0.55 |
| 53 | 21 | 1.6 | 350 | 5.5 | 58 | 0.65 |
| 54 | 22 | 1.0 | 140 | 4 | 52 | 0.40 |
| 55 | 23 | 1.0 | 140 | 5 | 51 | 0.35 |
| 56 | 24 | 1.0 | 150 | 4.5 | 40 | 0.35 |
| 57 | 25 | 1.0 | 170 | 4 | 53 | 0.40 |
| 58 | 26 | 1.0 | 200 | 5 | 52 | 0.35 |
| 59 | 27 | 1.0 | 200 | 5.5 | 52 | 0.30 |
| 60 | 28 | 1.0 | 200 | 5.5 | 53 | 0.30 |
| 61 | 29 | 1.0 | 200 | 5 | 53 | 0.35 |
| 62 | 30 | 1.0 | 200 | 5 | 52 | 0.40 |
| 63 | 31 | 1.0 | 200 | 5.5 | 53 | 0.40 |

Example  Compression  Dimensional  Blowing

-continued

| No. | Strain (%) | Change (%) | Marks | Stickiness | Precision |
|---|---|---|---|---|---|
| 34 | 5.60 | −0.05 | A | A | A |
| 35 | 8.55 | −0.05 | A | A | A |
| 36 | 3.10 | −0.05 | A | A | A |
| 37 | 5.50 | −0.05 | A | A | A |
| 38 | 4.70 | −0.05 | A | A | A |
| 39 | 5.15 | −0.05 | A | A | A |
| 40 | 3.75 | −0.05 | A | A | A |
| 41 | 4.20 | −0.05 | A | A | A |
| 42 | 2.80 | −0.05 | A | A | A |
| 43 | 3.65 | −0.05 | A | A | A |
| 44 | 2.95 | −0.05 | A | A | A |
| 45 | 2.75 | −0.05 | A | A | A |
| 46 | 7.15 | −0.05 | A | A | A |
| 47 | 7.30 | −0.05 | A | A | A |
| 48 | 3.15 | −0.05 | A | A | A |
| 49 | 3.25 | −0.05 | A | A | A |
| 50 | 2.20 | −0.05 | A | A | A |
| 51 | 2.60 | −0.05 | A | A | A |
| 52 | 4.30 | −0.05 | A | A | A |
| 53 | 4.25 | −0.05 | A | A | A |
| 54 | 5.50 | −0.05 | A | A | A |
| 55 | 2.70 | −0.05 | A | A | A |
| 56 | 3.05 | −0.05 | A | A | A |
| 57 | 5.70 | −0.05 | A | A | A |
| 58 | 3.55 | −0.05 | A | A | A |
| 59 | 2.80 | −0.05 | A | A | A |
| 60 | 2.20 | −0.05 | A | A | A |
| 61 | 3.30 | −0.05 | A | A | A |
| 62 | 2.35 | −0.05 | A | A | A |
| 63 | 2.05 | −0.05 | A | A | A |

COMPARATIVE EXAMPLE 4

A paste was prepared by mixing 45 parts of the same unsaturated polyether as used in Example 1, 5 parts of a polysiloxane modified with a polyether represented by the following average formula:

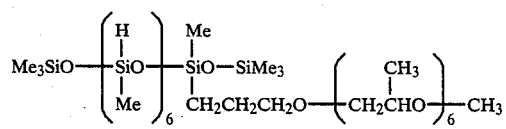

49.98 parts of quartz powder and 0.02 part of BHT. Equal amounts of this paste and the same catalyst paste as prepared in Example 4 (Si-H/AL ratio=1.0, Cpt=200 ppm) were kneaded. After 7 minutes at room temperature, a cured body having a rubbery elasticity was obtained. The contact angle of the cured body with water 56°, the compression set was 2.15%, the compression strain was 15.25%, and the dimensional change was 0.05%. When an impression of the interior of the oral cavity of a human body was collected, many blowing marks were observed on the impression surface (evaluation: C), the impression surface had a stickiness (evaluation: C), and a crown prepared based on this impression was not fit (evaluation: C).

We claim:

1. A curable composition, which comprises (A) an unsaturated polyether represented by the formula:

 (I)

or

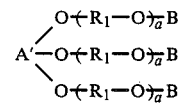 (I')

wherein A stands for a saturated hydrocarbon group having a valency of 2 and having 1 to 10 carbon atoms, A' stands for a saturated hydrocarbon group having a valency of 3 and having 3 to 10 carbon atoms, $R_1$ stands for a linear or branched alkylene group having 2 to 6 carbon atoms, with the proviso that if a is 2 or more, each $R_1$ may be the same or a different alkylene group and the polyether chain comprising units —O—$R_1$— can be in the form of a random polymer or a block polymer, a is an integer of from 1 to 300, and B stands for an unsaturated group represented by the formula

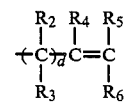

in which $R_2$, $R_3$, $R_4$, $R_5$ and $R_6$, which may be the same or different, stand for a hydrogen atom or an alkyl group having 1 to 10 carbon atoms and d is an integer of from 0 to 10, with the proviso that each B may be the same or a different group, (B) a siloxane-substituted polyether represented by the formula:

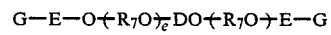 (II)

or

-continued

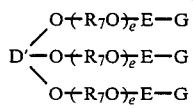 (II')

wherein D stands for a saturated hydrocarbon group having a valency of 2 and having 1 to 10 carbon atoms, D' stands for a saturated hydrocarbon group having a valency of 3 and having 3 to 10 carbon atoms, $R_7$ stands for a linear or branched alkylene group having 2 to 6 carbon atoms, with the proviso that if e is 2 or more, each $R_7$ may be the same or a different alkylene group and the polyether chain comprising units $-O-R_7-$ can be in the form of a random polymer or a block polymer, e is an integer of from 1 to 30, E stands for an alkylene group of the formula

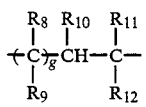

in which $R_8$, $R_9$, $R_{10}$, $R_{11}$ and $R_{12}$, which may be the same or different, stand for a hydrogen atom or an alkyl group having 1 to 10 carbon atoms and g is an integer of from 0 to 10, with the proviso that each E may be the same or a different alkylene group, and G stand for a siloxane group selected from the group consisting of (i)

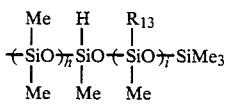

in which h and i are integers of from 0 to 8 satisfying the requirement of h+i=1 to 8, $R_{13}$ stands for a hydrogen atom or a methyl group, with the proviso that if i is 2 or more, each $R_{13}$ may be the same or a different group, and Me stands for a methyl group, (ii)

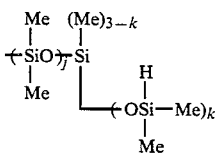

in which j is an integer of from 0 to 8, k is integer of from 1 to 3, with the proviso that j and k satisfy the requirement of j+k=1 to 9, and Me stands for a methyl group, and (iii)

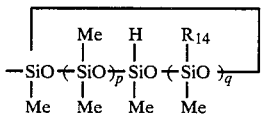

in which p and q are integers of from 0 to 4 satisfying the requirement of p+q=1 to 4 and $R_{14}$ has the same meaning as that of $R_{13}$, with the proviso that each G may be the same or a different siloxane group, and (C) at least one catalyst selected from the group consisting of platinum, chloroplatinic acid and platinum complexes.

2. A curable composition as set forth in claim 1, wherein the amount of the Si-H groups in the siloxane-substituted polyether (B) is 0.5 to 10 moles per mole of the total amount of the unsaturated groups of the polyether (A) and the amount of the platinum atom in the catalyst (C) is 0.1 ppm to 5% by weight based on the total amount of the unsaturated polyether (A) and the siloxane-substituted polyether (B).

3. A curable composition as set forth in claim 1, wherein the unsaturated polyether (A) is an unsaturated polyether represented by the following formula:

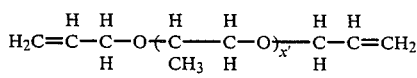

wherein x' is an integer of from 5 to 200.

4. A curable composition as set forth in claim 1, wherein the siloxane-substituted polyether (B) is a siloxane-substituted polyether represented by the following formula:

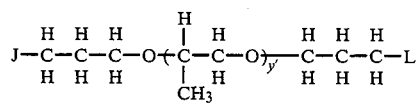

wherein y' is an integer of from 3 to 50, and J and L, which may be the same or different, stand for a group represented by the formula:

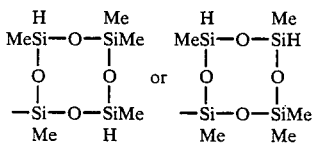

in which Me stands for a methyl group.

5. A dental impression material comprising a curable composition as set forth in claim 1.

6. A curable composition as set forth in claim 1, wherein the unsaturated polyether (A) is a polyether represented by the formula:

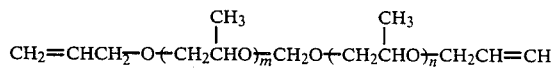

in which the sum of m and n is from 3 to 250.

7. A curable composition as set forth in claim 1, wherein the unsaturated polyether (A) is a polyether represented by the formula:

$$CH_2=CHCH_2O\left(CH_2CHO\overset{CH_3}{|}\right)_l CH_2CH=CH_2;$$

$$CH_2=CHCH_2O\left(CH_2CHO\overset{CH_3}{|}\right)_m CH_2O\left(CH_2CHO\overset{CH_3}{|}\right)_n CH_2CH=CH_2;$$

$$CH_2=CHCH_2O(CH_2CH_2O)_m\left(CH_2CHO\overset{CH_3}{|}\right)_n CH_2CH=CH_2;$$

$$CH_2=CHCH_2O(CH_2CH_2O)_m(CH_2CH_2CH_2CH_2O)_n CH_2CH=CH_2;$$

$$CH_2=CHO\left(CH_2CHO\overset{CH_3}{|}\right)_l CH=CH_2;$$

$$CH_2=CHO\left(CH_2CHO\overset{CH_3}{|}\right)_m CH_2O\left(CH_2CHO\overset{CH_3}{|}\right)_n CH=CH_2;$$

$$CH_2=CHO(CH_2CH_2O)_m\left(CH_2CHO\overset{CH_3}{|}\right)_n CH=CH_2;$$

$$CH_2=CHO(CH_2CH_2O)_m(CH_2CH_2CH_2CH_2O)_n CH=CH_2;$$

$$CH_2=CHCO\overset{CH_3}{\underset{CH_3}{|}}\left(CH_2CHO\overset{CH_3}{|}\right)_l CCH=CH_2\overset{CH_3}{\underset{CH_3}{|}};$$

$$CH_2=CHCO\overset{CH_3}{\underset{CH_3}{|}}\left(CH_2CHO\overset{CH_3}{|}\right)_m CH_2O\left(CH_2CHO\overset{CH_3}{|}\right)_n CCH=CH_2\overset{CH_3}{\underset{CH_3}{|}};$$

$$CH_2=CHCO\overset{CH_3}{\underset{CH_3}{|}}(CH_2CH_2O)_m\left(CH_2CHO\overset{CH_3}{|}\right)_n CCH=CH_2\overset{CH_3}{\underset{CH_3}{|}};$$

$$CH_2=CHCO\overset{CH_3}{\underset{CH_3}{|}}(CH_2CH_2O)_m(CH_2CH_2CH_2CH_2O)_n CCH=CH_2\overset{CH_3}{\underset{CH_3}{|}};$$

$$CH_2=CH(CH_2)_4O\left(CH_2CHO\overset{CH_3}{|}\right)_l (CH_2)_4 CH=CH_2;$$

$$CH_2=CCH_2O\overset{CH_3}{|}\left(CH_2CHO\overset{CH_3}{|}\right)_m (CH_2CH_2CH_2CH_2O)_n CH_2C=CH_2\overset{CH_3}{|};$$

$$CH_3CH=CHCH_2O(CH_2CH_2CH_2CH_2O)_n CH_2CH=CHCH_3;$$

-continued
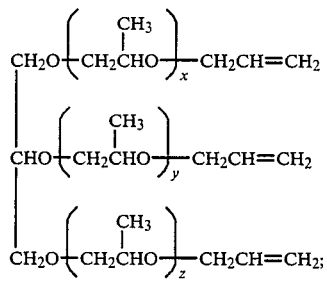
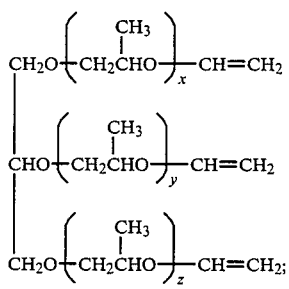
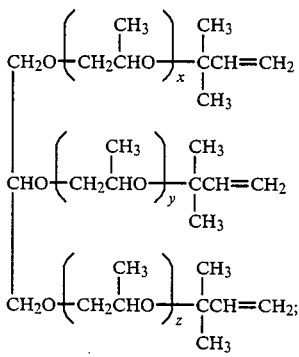
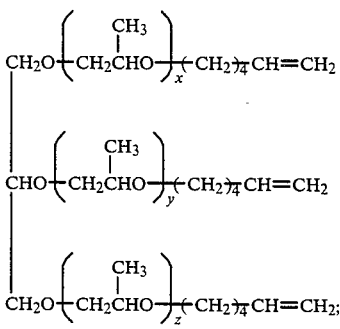
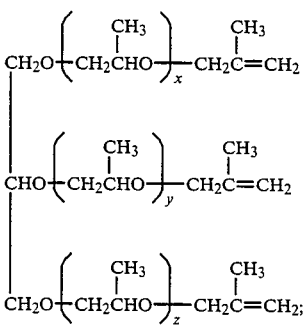

-continued
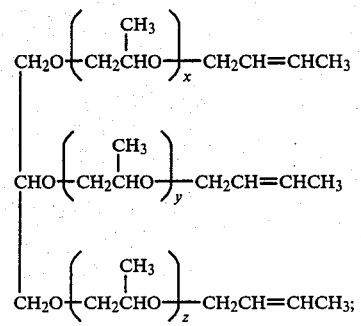
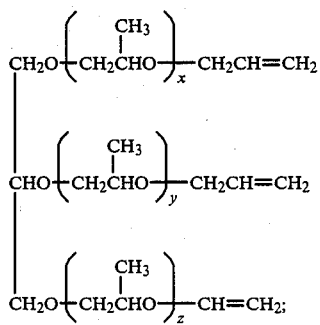
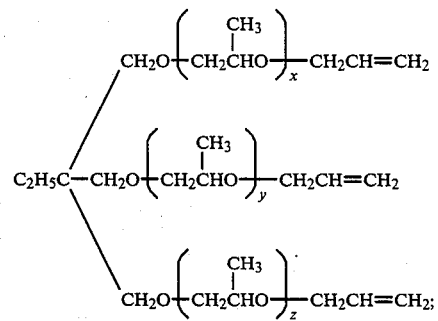
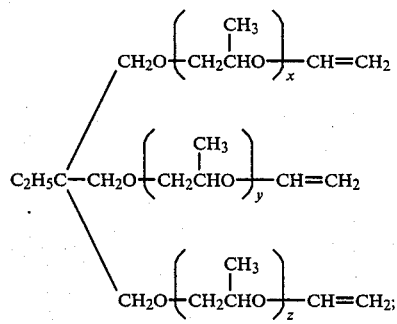

-continued

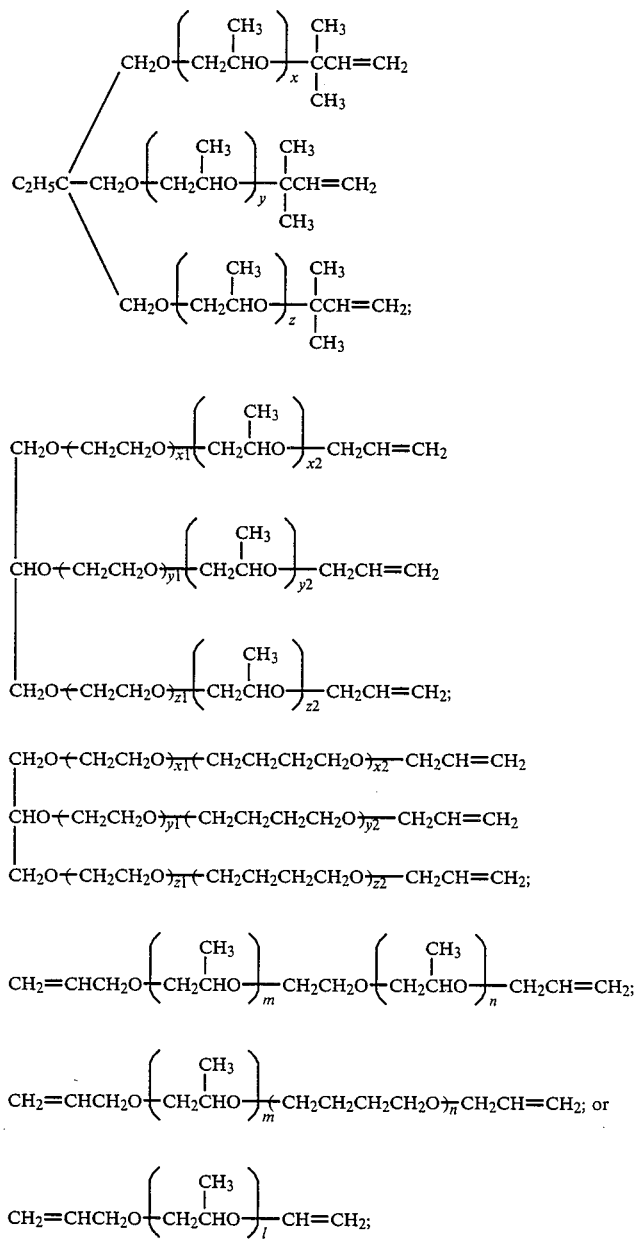

wherein
l is an integer of from 3 to 250;
m, n, x, y and z are integers of at least 1; and
x1, y1, z1, x2, y2 and z2 are integers of at least 0;
with the proviso that the sum of m and n is from 3 to 250, the sum of x, y and z is from 3 to 250, the sum of x1 and x2 is at least 1, the sum of y1 and y2 is at least 1, the sum of z1 and z2 is at least 1, and the sum of x1, x2, y1, y2, z1 and z2 is up to 250.

8. A curable composition as set forth in claim 1, wherein the siloxane-substituted polyether (B) is represented by the formula:

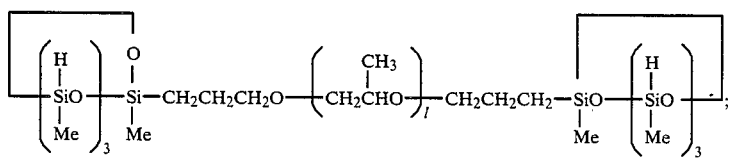

-continued
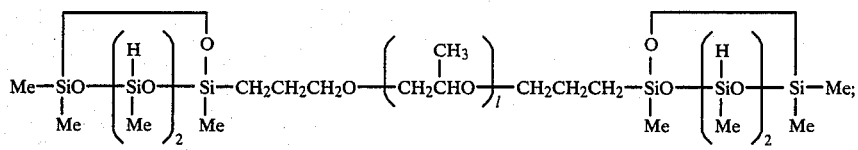
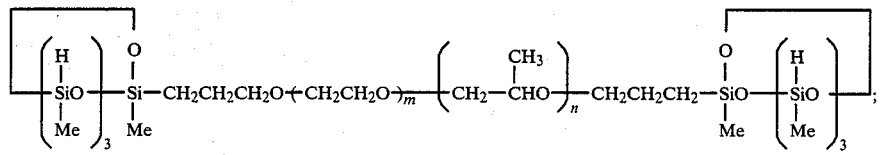
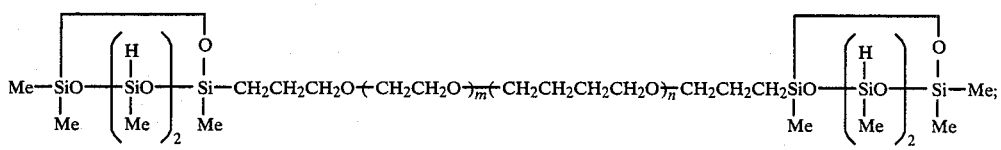
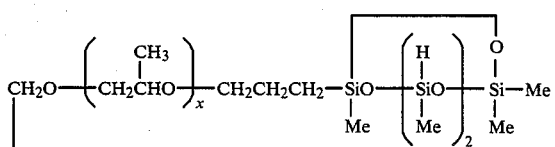
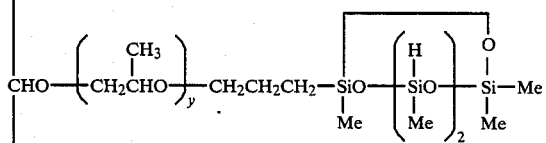
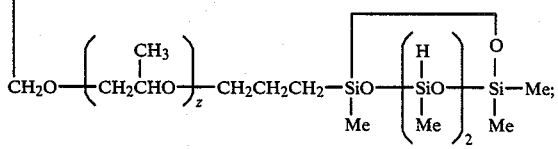
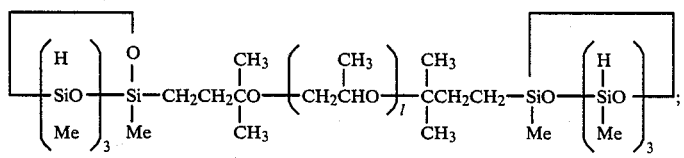
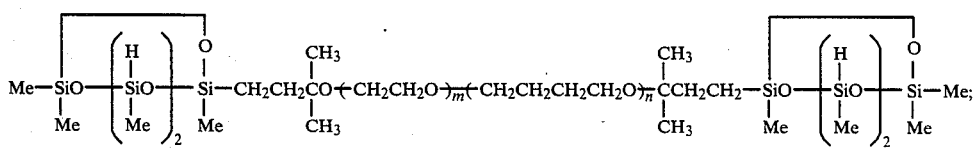

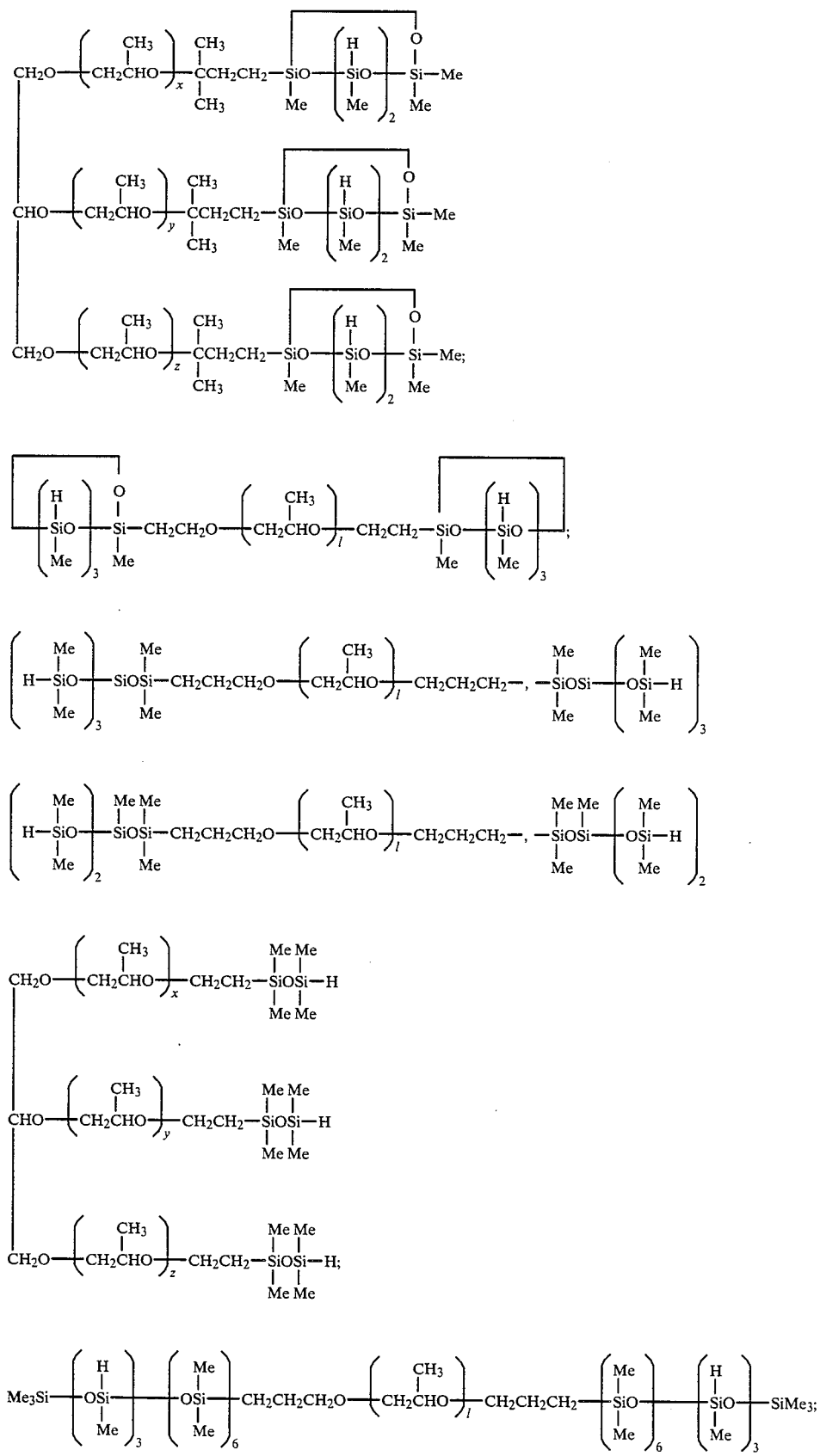

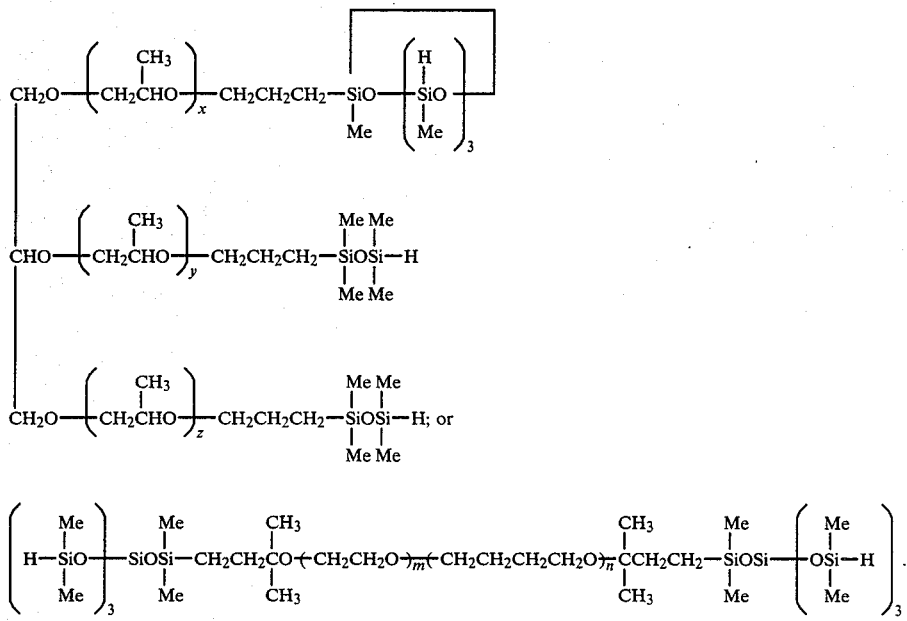

wherein
Me is a methyl group;
l is an integer of from 3 to 60; and
m, n, x, y and z are integers of at least 1;
with the proviso that the sum of m and n is from 3 to 60 and the sum of x, y and z is from 3 to 90.

9. A curable composition as set forth in claim 1, wherein A comprises at least two carbon atoms and said groups $BO(R_1-O)_{\overline{a}}$ and $B(O-R_1)_{\overline{a}}O-$ are not bonded to the same carbon atom.

10. A curable composition as set forth in claim 1, wherein each of said groups $-O(R_1-O)_aB$ is bonded to a different carbon atom of said group $A'$.

* * * * *